US007771721B2

(12) United States Patent
Davis-Smyth et al.

(10) Patent No.: US 7,771,721 B2
(45) Date of Patent: *Aug. 10, 2010

(54) METHODS FOR USING CHIMERIC VASCULAR ENDOTHELIAL GROWTH FACTOR RECEPTOR PROTEINS

(75) Inventors: Terri Lynn Davis-Smyth, Foster City, CA (US); Helen Hsifei Chen, Daly City, CA (US); Leonard Presta, San Francisco, CA (US); Napoleone Ferrara, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/104,825

(22) Filed: Apr. 17, 2008

(65) Prior Publication Data

US 2009/0010933 A1 Jan. 8, 2009

Related U.S. Application Data

(60) Continuation of application No. 11/537,623, filed on Sep. 30, 2006, which is a continuation of application No. 11/043,693, filed on Jan. 26, 2005, now abandoned, which is a continuation of application No. 10/105,901, filed on Mar. 20, 2002, now Pat. No. 6,897,294, which is a continuation of application No. 09/348,886, filed on Jul. 1, 1999, now Pat. No. 6,383,486, which is a division of application No. 08/643,839, filed on May 7, 1996, now Pat. No. 6,100,071.

(51) Int. Cl.
A61K 38/18 (2006.01)
C07K 14/71 (2006.01)
C12N 15/62 (2006.01)

(52) U.S. Cl. .................. 424/134.1; 424/192.1; 514/2; 530/350; 536/23.4

(58) Field of Classification Search .................. None
See application file for complete search history.

(56) References Cited

U.S. PATENT DOCUMENTS

| | | | |
|---|---|---|---|
| 4,456,550 A | 6/1984 | Dvorak et al. |
| 5,008,196 A | 4/1991 | Connolly et al. |
| 5,036,003 A | 7/1991 | Olander et al. |
| 5,185,438 A | 2/1993 | Lemischka |
| 5,240,848 A | 8/1993 | Keck et al. |
| 5,776,755 A | 7/1998 | Alitalo et al. |
| 5,844,099 A | 12/1998 | Stahl et al. |
| 5,861,484 A | 1/1999 | Kendall et al. |
| 5,952,199 A | 9/1999 | Davis-Smyth et al. |
| 6,100,071 A | 8/2000 | Davis-Smyth et al. |
| 6,383,486 B1 | 5/2002 | Davis-Smyth et al. |
| 6,472,179 B2 | 10/2002 | Stahl et al. |
| 6,833,349 B2 | 12/2004 | Xia et al. |
| 6,897,294 B2 | 5/2005 | Davis-Smyth et al. |
| 7,070,959 B1 | 7/2006 | Papadopoulos et al. |
| 7,087,411 B2 | 8/2006 | Daly et al. |
| 7,279,159 B2 | 10/2007 | Daly et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| 7,374,757 B2 | 5/2008 | Papadopoulos et al. |
| 7,374,758 B2 | 5/2008 | Papadopoulos et al. |
| 7,396,664 B2 | 7/2008 | Daly et al. |
| 7,399,612 B2 | 7/2008 | Daly et al. |
| 7,521,049 B2 | 4/2009 | Wiegand et al. |
| 7,524,499 B2 | 4/2009 | Papadopoulos et al. |
| 2004/0014667 A1 | 1/2004 | Daly et al. |
| 2004/0266686 A1 | 12/2004 | Xia et al. |
| 2005/0281831 A1 | 12/2005 | Davis-Smyth et al. |
| 2007/0128695 A1 | 6/2007 | Davis-Smyth et al. |
| 2008/0194460 A1 | 8/2008 | Papadopoulos et al. |
| 2009/0062200 A1 | 3/2009 | Daly et al. |
| 2009/0081217 A1 | 3/2009 | Papadopoulos et al. |
| 2009/0155899 A1 | 6/2009 | Papadopoulos et al. |
| 2009/0234103 A1 | 9/2009 | Davis-Smyth et al. |

FOREIGN PATENT DOCUMENTS

EP 1183353 4/2005

(Continued)

OTHER PUBLICATIONS

Lee et al., 1996, *Proc. Natl. Acad. Sci. USA*, 93:1988-1992 "Vascular endothelial growth factor-related protein: A ligand and specific activator of the tyrosine kinase receptor Flt4."
Leung et al., 1989, *Science*, 246:1306 "Vascular endothelial growth factor is a secreted angiogenic mitogen."
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.
Park et al., 1994. *J. Biol. Chem.*, 269:25646-25654 "Placenta Growth Factor: Potentiation of vascular endothelial growth factor bioactivity, in vitro and in vivo and high affinity binding to Flt-1 but not to Flk-1/KDR."

(Continued)

*Primary Examiner*—Christine J Saoud
*Assistant Examiner*—Jon M Lockard
(74) *Attorney, Agent, or Firm*—Jones Day

(57) ABSTRACT

The present invention is directed to novel chimeric VEGF receptor proteins comprising amino acid sequences derived from the vascular endothelial growth factor (VEGF) receptors flt-1 and KDR, including the murine homologue to the human KDR receptor FLK-1, wherein said chimeric VEGF receptor proteins bind to VEGF and antagonize the endothelial cell proliferative and angiogenic activity thereof. The present invention is also directed to nucleic acids and expression vectors encoding these chimeric VEGF receptor proteins, host cells harboring such expression vectors, pharmaceutically acceptable compositions comprising such proteins, methods of preparing such proteins and to methods utilizing such proteins for the treatment of conditions associated with undesired vascularization.

44 Claims, 7 Drawing Sheets

FOREIGN PATENT DOCUMENTS

| EP | 0907733 | 5/2006 |
|---|---|---|
| EP | 1666499 | 6/2006 |
| EP | 1710254 | 10/2006 |
| WO | WO 91/08298 | 6/1991 |
| WO | WO 92/14748 | 9/1992 |
| WO | WO 92/17486 | 10/1992 |
| WO | WO 94/11499 | 5/1994 |
| WO | WO 94/21679 | 9/1994 |
| WO | WO 95/21868 | 8/1995 |
| WO | WO 95/33050 | 12/1995 |
| WO | WO 95/33772 | 12/1995 |
| WO | WO 97/44453 | 11/1997 |
| WO | WO 00/75319 | 12/2000 |

OTHER PUBLICATIONS

Plowman et al., 1994, *DN&P*. 7(6):334-339 "Receptor Tyrosine Kinases as Targets for Drug Intervention."

Quinn et al., 1993, *Proc. Natl. Acad. Set USA*. 90:7533-7537 "Fetal liver kinase 1 is a receptor for vascular endothelial growth factor and is selectively expressed in vascular endothelium."

Rockwell et al., 1995, *Molecular and Cellular Differentiation*. 3(1):91-109 "In vitro Neutralization of Vascular Endothelial Growth Factor Activation of Flk-1 by a Monoclonal Antibody."

Schulz et al., 1979, *Principles of Protein Structure*, Springer-Verlag: New York, NY, pp. 14-16.

Shibuya et al., 1990, *Oncogene*. 5:519-524 "Nucleotides Sequence and Expression of a Novel Human Receptor-Type/tyrosine Kinase Gene (flt) Closely Related to the fms Family."

Terman et al., *Oncogene*, 6:1677-1683 "Identification of a new endothelial cell growth factor receptor tyrosine kinase," 1991.

Tessler et al., 1994, *The Journal of Biological Chemistry*, 269(17): 12456-12461 "Heparin Modulates the Interaction of VEGF 165 with soluble and Cell Associated flk-1 Receptors."

Tischer et al., 1991. *The Journal of Biological Chemistry*, 266(18): 11947-11954 "The Human Gene for Vascular Endothelial Growth Factor."

Tischer et al., 1989, *Biochemical and Biophysical Research Communications*. 165(3): 1198-1206 "Vascular Endothelial Growth Factor: A New Member of the Platelet-Derived Growth Factor Gene Family."

Wells. J.A. (1990). Additivity of mutational effects in proteins. Biochemistry. 29(37):8509-8517.

Weidner et al., 1991. *New Engl. J. Med.*, 324:1-8 "Tumor angiogenesis and metastasis—correlation in invasive breast carcinoma."

Wiesmann et al., 1997, *Cell*. 91:695-701 "Crystal Structure at 1.7 A Resolution of VEGF in Complex with Domain 2 of the Flt-1 Receptor."

Partial European Search Report, Mailing Date: May 18, 2006.

U.S. Appl. No. 12/104,894, filed Apr. 17, 2008, Davis-Smyth et al.

Aiello et al., 1995, *Proc. Natl. Acad. Sci. USA*, 92(23)L 10457-10461 "Suppression of Retinal Neovascularization in vivo by Inhibition of Vascular Endothelial Growth Factor (VEGF) Using Soluble VEGF-Receptor Chimeric Proteins."

Borg et al., *Oncogene*, 10(5):973-984 "Biochemical characterization of Two Isoforms of FLT4, a VEGF Receptor-Related Tyrosine Kinase," (1995).

Chamow et al., 1996, *TIBTECH*, 14:52-60 "Immunoadhesins: principles and applications."

Cheon et al., 1994, *Proc. Natl. Acad. Sci. USA*, 91:989-993 "High-Affinity Binding Sites for Related Fibroblast Growth Factor Ligands Reside within Different Receptor Immunoglobulin-like Domains."

Creighton, 1984, *Proteins*, WH Freeman and Company: New York, NY, pp. 223-227.

Cunningham, 1997, *Biochemical and Biophysical Research Communications*, 231:596-599 "Identification of the Extracellular Domains of Flt-1 that Mediate Ligand Interactions."

Davis-Smyth et al., 1996, *EMBO J.*, 15:4919-4927 "The second immunoglobulin-like domain of the VEGF tyrosine kinase receptor Flt-1 determines ligand binding and may initiate a signal transduction cascade."

DeVries et al., 1992, *Science*, 225:989-991 "The fms-like tyrosine kinase, a receptor for vascular endothelial growth factor."

Ferrara et al., 1989, *Biochem. Biophys. Res. Comm.*, 161: 851-858 "Pituitary follicular cells secrete a novel heparin-binding growth factor specific for vascular endothelial cells."

Ferrara et al., 1991, *Journal of Cellular Biochemistry*, 47:211-218 "The Vascular Endothelial Growth Factor Family of Polypeptides."

Folkman et al., 1989, *Nature*, 339:58-61 "Induction of angiogenesis during the transition from hyperplasia to neoplasia."

Fuh et al., 1998. *J. Biol. Chem.*, 273:11197-11204 "Requirements for Binding and Signaling of the Kinase Domain Receptor for Vascular Endothelial Growth Factor."

Heidaran et al., 1995, *FASEB J.*, 9:140-145 "PDGFR-IgG Chimera Demonstrates that Human PDGFR Ig-like Domains 1 to 3 are Sufficient for High Affinity PDGF BB Binding."

Holash et al., 2002. *Proc. Natl. Acad. Sci. USA*, 99:11393-11398 "VEGF-Trap: A VEGF blocker with potent antitumor effects."

Kendall et al., 1993, *Proc. Natl. Acad. Sci. USA*, 90:10705-10709 "Inhibition of Vascular Endothelial Cell Growth Factor Activity by an Endogenously Encoded Soluble Receptor."

Kim et al., 1993. *Nature*, 362:841-844 "Inhibition of vascular endothelial growth factor-induced angiogenesis suppresses tumour growth in vivo."

Klein. 1982. *Immunology : The Science of Self-Nonself Discrimination*, Wiley-Interscience: New York, NY. pp. 160-160 and 190-191.

International Preliminary Examination Report for PCT/US97/07694, dated Jul. 23, 1998.

Extended European Search Report for European Patent Application No. 06002727.3, dated Mar. 12, 2007.

Keyt et al., 1996, "Identification of vascular endothelial growth factor determinants for binding KDR and FLT-1 receptors. Generation of receptor-selective VEGF variants by site-directed mutagenesis," J. Biol. Chem. 271:5638-5646.

Mahadevan et al., 1995, "Structural role of extracellular domain 1 of alpha-platelet-derived growth factor (PDGF) receptor for PDGF-AA and PDGF-BB binding," J. Biol. Chem. 270:27595-27600.

```
              DOMAIN 1
flt1    1   MVSYWDTGVLLC-ALLSCLLLTGSS---SGSKLKDPELSLKGTQHIMQAGQTLHLQCRGEAAHKWSLPEMV------SKESERLSITKSACGRNGKQFCS
KDR     1   M----ESKVLLAVALWLCVETRAASVGLPSVSLDLPRLSIQKDILTIKANTLQITCRGQRDLDWLWPNNQ-------SGSEQRVEVTECSDG---LFCK
FLT4    1   M----QRGAALCLRLWLCLGLDGLV---SGYSMTPPTLNITEESHVIDTGDSLSISCRGQHPLEWAWPGAQEAPATGDKDSEDTGVVRDCEGTDARPYCK DOMAIN 2
flt1   91   TLTLNTAQANHTGFYSCKYLAVPTSKKKETESAIYIFISDTGRPFVEMYSEIPEIIHM--TEGRELVIPCRVTSPNITVTL-KKFPLDTLIPDGKRIIWD
KDR    87   TLTIPKVIGNDTGAYKCFYR------ETDLASVIYVYVQDYRSPFIASVSDQHGVVYITENKNKTVVIPCLGSISNLNVSLCARYPEKRFVPDGNRISWD
FLT4   95   VLLLHEVHANDTGSYVCYYKYIKARIEGTTAASSYVFRDFEQPFI----NRKDAMVPCLVSIPGLNVTL--RSQSSVLMPDGQEVVWD DOMAIN 3
flt1  188   SRKGFIISNATYKEIGLLTCEATVNGHLYKTN--YLTHRQTNTIIDVQISTPRPVKLLRGHTLVLNCTATTPLNTRVQMTWSYPDEKNKRAS--VRRRIDQ
KDR   181   SKKGFTIPSYMISYAGMVFCEAKINDESYQSIMYIVVVGYRIYDVVLSPSHGIELSVGEKLVLNCTARTELNVGIDFNWEYPSSKHQHKKLVNRDLKTQ
FLT4  187   DRRGMLVSTPLLHDALYLQCETTWGDQDFLSNPFLVHITGNELYDIQLLPRKSLELLVGEKLVLNCTVWAEFNSGVTFDMDYPGKQAERGKWVPERRSQQ DOMAIN 4
flt1  285   SNSHANIFYSVLTIDKMQNKDKGLYTCRVRSGPSFKSVNTSVHIYDKAFITVKHRKQQVLETVAGKRSYRLSMKVKAFPSPEVVWLKDGLPATEKSARYL-
KDR   281   SGSEMKKFLSTLTIDGVTRSDQGLYTCAASSGLMTKKNSTFVRVHEKPFVAFGSGMESLVEATVGER-VRIPAKYLGYPPPEIKWYKNGIPLESN--HTI
FLT4  287   THTELS---SILTIHNVSQHDLGSYVCKANNGIQRFRESTEVIVHENPFISVEWLKGPILEATAGDELVKLPVKLAAYPPPEFQWYKDGKQALSGR--H--

DOMAIN 5
flt1  385   TRGYSLIIKDVTEEDAGNYTILLSIKQSNVFKNLTATLIVNVKPQIYEKAVSSFPDPALYPLGSRQILTCTAYGIPQP--TIKWFWH---PCNHNHSEARC
KDR   378   KAGHVLTIMEVSERDTGNYTVILTNPISKEKQSHVVSLVVYVPPQIGEKSLIS--PVDSYQYGTTQTLTCTVYAIPPPHHIHWYWQLEEECANEPSQAVS
FLT4  380   -SPHALVLKEVTEASTGTYTLALWNSAAGLRRNISELVVNVPPQIHEKEASS--P-SIYSRHSRQALTCTAYGVPLPLSIQWHWRPWTPCKMFAQRSLR
```

FIG._1-A

```
                                                      DOMAIN 6
flt1  481  DFCSN----NEESFILDADSNMGNRIESITQRMAIIEGKNKMASTLVVADSRISGIYICIASNKVGTVGRNISFYITPVPNGFHVNL--EKMPTEGEDLK
KDR   476  VTNPY----PCEEMRSVEDFQGGNKIEVNKNQFALIEGKNKTVSTLVIQAANVSALYKCEAVNKVGRGERVISFHVTRGPE---ITLQPDMQPTEQESVS
FLT4  476  RQQQDLMPQCRDWRAVTTQDAVNPIESLDTWTEFVEGKNKTVSKLVIQNANVSAMYKCVVSNKVGQDERLIYFYVTIPDGFTIESKPSEELLEGQPVL flt1  575  LSCTVNKFLYRDVTWILLR----TVNNRTMHYSISKQ------KVAIT------KEHSITNLTIMNVSLQDSGTYACRARNVTGEEILQKKEITIRDQ
KDR   569  LWCTADRSTFENLTWYKLGPQPLPIHVGELPTPVCKNLDTL-WKLNATM----FSNSTNDILIMELKNASLQDQGDYVCLAQDRKTKKRHCVVRQLTVLER
FLT4  576  LSCQADSYKYEHLRWYRLNLSTLHDAHGNPLLLDCKNVHLFATPLAASLEEVAPGARHATLSLSIPRVAPEHEGHYVCEVQDRRSHDKHCHKKYLSVQAL
                                                                                                   DOMAIN 7
flt1  659  EAPYLLRNLSDHTVAISSSTTLDCHANGVPEPQITWFKNNHKIQQEPGIILGPGSSTLFIERVTEEDEGVYHCKATNQKGSVESSAYLTVQGTSDKSN--
KDR   665  VAPTITGNLENQTTSIGESIEVSCTASGNPPPQIMWFKDNETLVEDSGIVLKDGNRNLTIRRVRKEDEGLYTCQACSVLGCAKVEAFFIIEGAQEKTNLD
FLT4  676  EAPRLTQMLTDLLVNVSDSLEMQCLVAGAHAPSIVWYKDERLLEEKSGVDLADSNQKLSIQRVREEDAGRYLCSVCNAKGCVNSSASVAVEGSEDKGSME flt1  757  -FE
KDR   765  PFE
FLT4  776  -VT
```

*FIG.__1-B*

```
                                    Bgl II                                    Age I
DOMAIN 1: A AAA TTA AAA GAT CCA GAT CTG AGT...ATC TAT ATA TTT ATT AGT GAT ACC GGT AGA CCT TTT
            K   L   K   D   P   D   L   S(35)  I(124)Y   I   F   I   S   D   T   G   R   P   F
                                        (E)
                            Kas I                              Kpn I
DOMAIN 2: G AAG GAA ACA GAA GGC GCC ATC TAT ATA TTT ATT....CGA GGT ACC AAT ACA ATC ATA G
            K   E   T   E   G   A   I   Y   I   F   I(128)   R(224)G   T   N   T   I   I
                            (S)                                  (Q)
                        Bgl II                                    Age I
DOMAIN 3: CA AAC TAT CTC ACA CAT AGA TCT ACC...GTG CAT ATA TAT GAT ACC GGT TTC ATC ACT GTG AAA C
            N   Y   L   T   H   R   S   T(226)  V(326)H   I   Y   D   T   G   F   I   T   V   K
                                (Q)                              (K)  (A)
                Bbr PI                                              Bgl II
DOMAIN 4: GTT AAC ACC TCA GTG CAC GTG TAT GAT....GTC AAT GTG AAA CCC CAG ATC TAC GAA AAG GCC GTG TC
            V   N   T   S   V   H   V   Y   D(330)  V(424)N   V   K   P   Q   I   Y   E   K   A   V
                            (I)
                Nhe I                                        Bgl II
DOMAIN 5: A AAC CTC ACT GCC ACG CTA GCT GTC AAT GTG...TTT TAT ATC ACA GAT CTG CCA AAT GGG TTT CAT
            N   L   T   A   T   L   A   V   N   V(426)  F(550)Y   I   T   D   L   P   N   G   F   H
                            (I)                                      (V)
                    Bst 1107I                              Bgl II
DOMAIN 6: GTG GGA AGA AAC ATA AGC TTT GTA TAC...ATT ACA ATC AGA TCT CAG GAA GCA CCA TAC
            V   G   R   N   I   S   F   V   Y(552)  I(653)T   I   R   S   Q   E   A   P   Y
                                (Y)  (I)                      (D)
                Bsi WI                                Kpn I
DOMAIN 7: C CAG AAG AAA GAA ATT ACC GTA CGA GAT...CTC ACT GTT CAA GGT ACC TCG GAC AAG TCT AAT
            Q   K   K   E   I   T   V   R   D(657)  L(746)T   V   Q   G   T   S   D   K   S   N
                                (I)

FIG._2
```

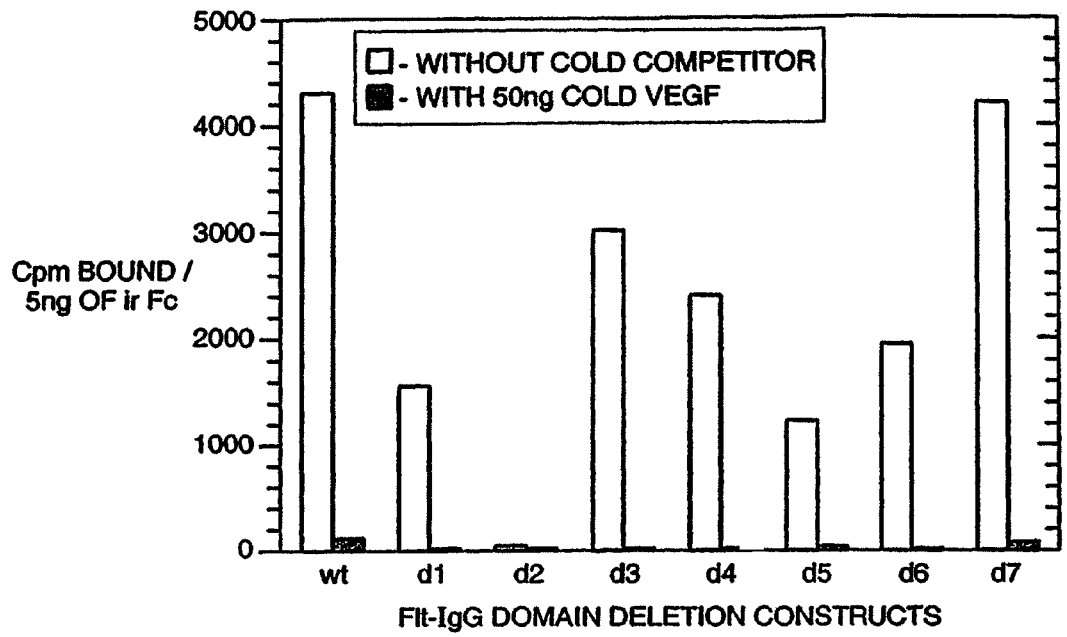
FIG._3
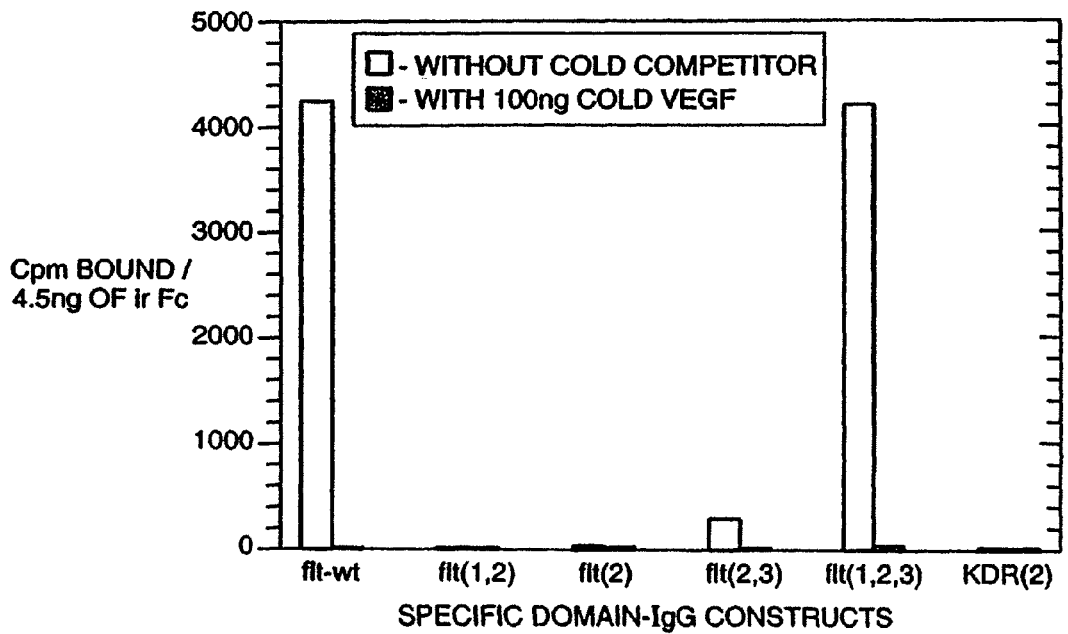
FIG._4

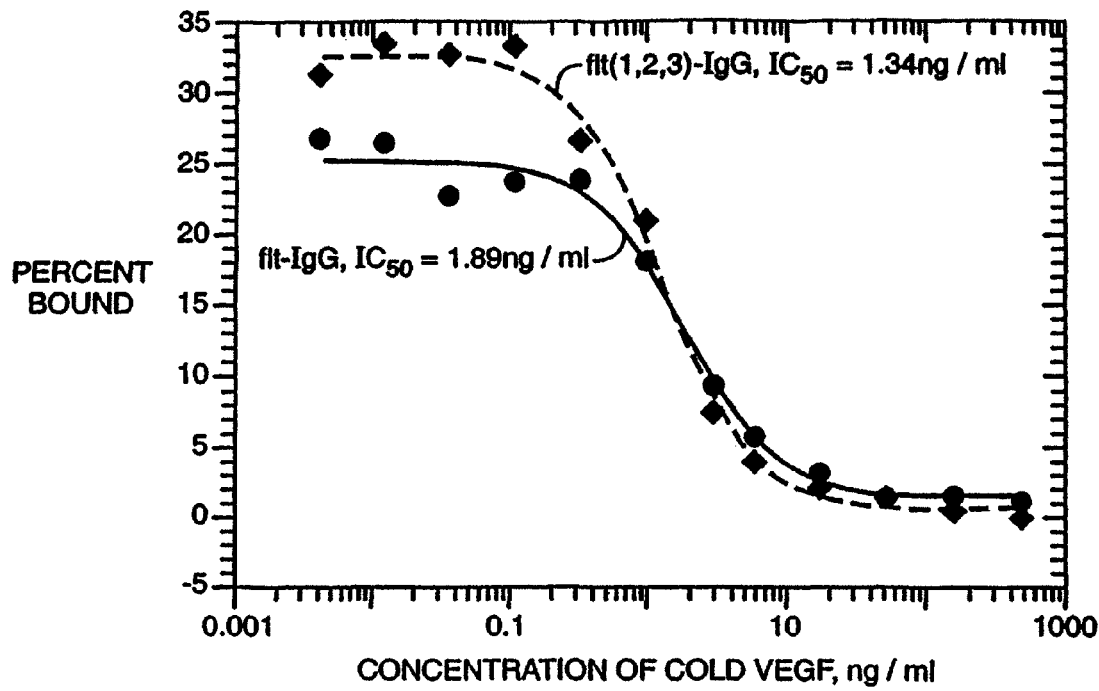
FIG._5
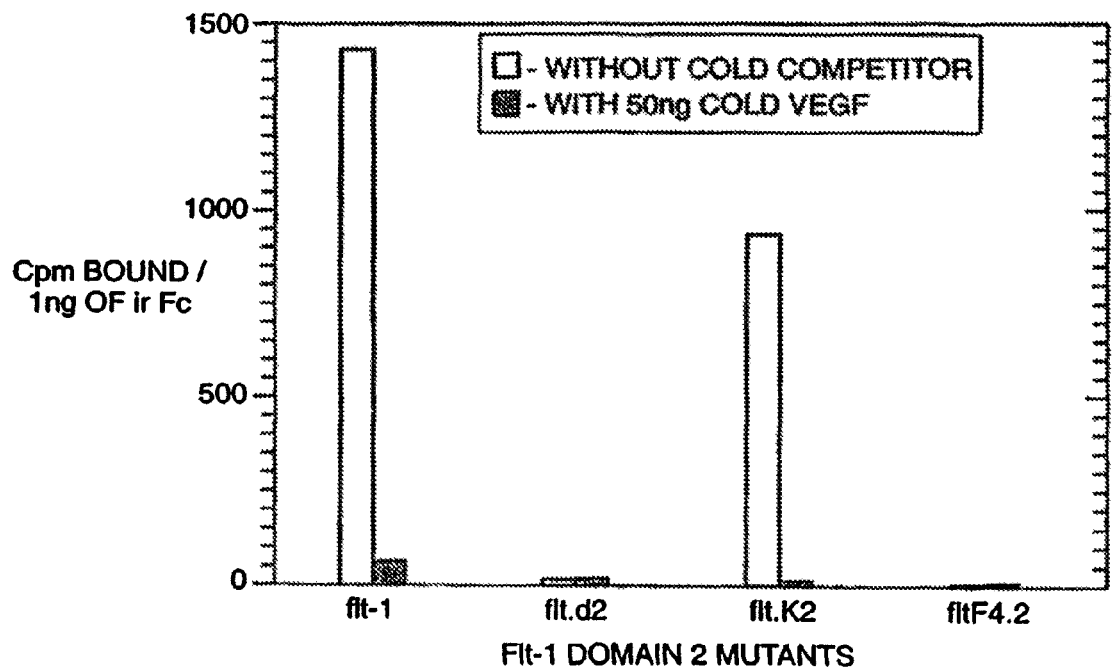
FIG._6

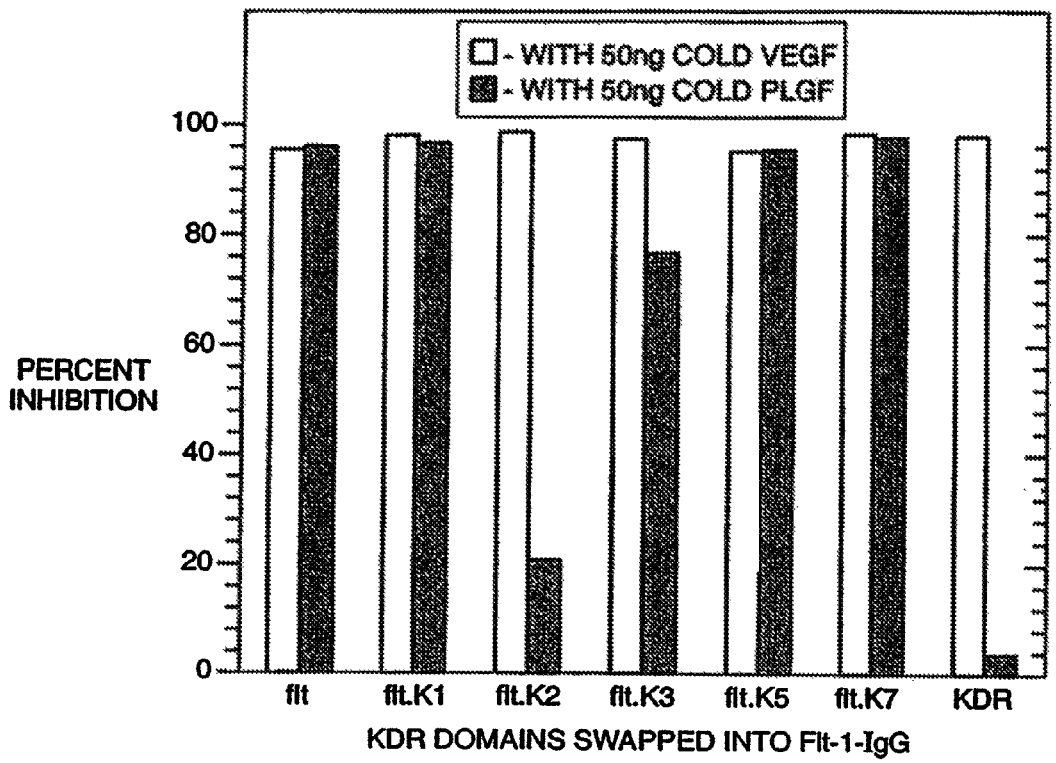

FIG._7

MQRGAALCLRLWLCLGLLDGLVSGYSMTPPTLNITEESHVIDTGDSLSISCRGQHPLEWA
WPGAQEAPATGDKDSEDTGVVRDCEGTDARPYCKVLLLHEVHANDTGSYVCYYKYIKARI
EGTTAASSYVFVRDFEQPPINKPDTLLVNRKDAMWVPCLVSIPGLNVTLRSQSSVLWPDG
QEVVWDDRRGMLVSTPLLHDALYLQCETTWGDQDFLSNPFLVHITGNELYDIQLLPRKSL
ELLVGEKLVLNCTVWAEFNSGVTFDWDYPGKQAERGKWVPERRSQQTHTELSSILTIHNV
SQHDLGSYVCKANNGIQRFRESTEVIVHENPFISVEWLKGPILEATAGDELVKLPVKLAA
YPPPEFQWYKDGKALSGRHSPHALVLKEVTEASTGTYTLALWNSAAGLRRNISLELVVNV
PPQIHEKEASSPSIYSRHSRQALTCTAYGVPLPLSIQWHWRPWTPCKMFAQRSLRRRQQQ
DLMPQCRDWRAVTTQDAVNPIISLDTWTEFVEGKNKTVSKLVIQNANVSAMYKCVVSNKV
GQDERLIYFYVTTIPDGFTIESKPSEBLLEGQPVLLSCQADSYKYEHLRWYRLNLSTLHD
AHGNPLLLDCKNVHLFATPLAASLEEVAPGARHATLSLSIPRVAPEHEGHYVCEVQDRRS
HDKHCHKKYLSVQALEAPRLTQNLTDLLVNVSDSLEMQCLVAGAHAPSIVWYKDERLLEE
KSGVDLADSNQKLSIQRVREEDAGRYLCSVCNAKGCVNSSASVAVEGSEDKGSMEIVILV
GTGVIAVFFWVLLLLIFCNMRRPANADIKTGYLSIIMDPGEVPLEEQCEYLSYDASQWEF
PRERLHLGRVLGYGAFGFVVEASAFGIHKGSSCDTVAVKMLKEGASASEHRALMSELKIL
IHIGNHLNVVNLLGACTKPQGPLMVIVEFCKYGNLSNFLRAKRDAFSPCAEKSPEQRGRF
RAMVELARLDRRRPGSSDRVLFARFSKSEGGARRASPDQEAEDLWLSPLTMEDLVCYSFQ
VARGMEFLASRKCIHRDLAARNILLSESDVVKICDFGLARDIYKDPDYVRKGSARLPLKW
MAPESIFDKVYTTQSDVMSFGVLLWEIFSLGASPYPGVQINEEFCQRLRDGTRMRAPELA
TPAIRRIMLNCWSGDPKARPAFSEVLEILGDLLQGRGLQEBEEVCMAPRSSQSSEEGSPS
QVSTMALHIIQADAEDSPPSLQRHSLAARYYNWVSPPGCLARGAETRGSSRMKTPEEFPM
TPTTYKGSVDNQTDSGMVLASEEFEQIESRHRQESGFSCKGPGQNVAVTRAHPDSQGRRR
RPERGARGGQVFYNSEYGELSEPSEEDHCSPSARVTPPTDNSY

FIG._8

MQRGAALCLRLWLCLGLLDGLVSGYSMTPPTLSLKGTQHIMQAGQTLHLQCRGEAAHKWS
LPEMVSKESRRLSITKSACGRNGKQFCSTLTLNTAQANHTGFYSCKYLAVPTSKKKETES
AIYIFISDTGRPFVEMYSEIPEIIHMTEGRELVIPCRVTSPNITVTLKKFPLDTLIPDGK
RIIWDSRKGFIISNATYKEIGLLTCEATVNGHLYKTNYLTHRQTNTIIDVQISTPRPVKL
LRGHTLVLNCTATTPLNTKVQMTWSYPDEKNKRASVRRRIDQSNSHANIFYSVLTIDKMQ
NKDKGLYTCRVRSGPSFKSVNTSVRVHENPFISVEWLKGPILEATAGDELVKLPVKLAAY
PPPEFQWYKDGKALSGRHSPHALVLKEVTEASTGTYTLALWNSAAGLRRNISLELVVNVP
PQIHEKEASSPSIYSRHSRQALTCAYGVPLPLSIQWHWRPWTPCKMFAQRSLRRRQQQD
LMPQCRDWRAVTTQDAVNPIESLDTWTEFVEGKNKTVSKLVIQNANVSAMYKCVVSNKVG
QDERLIYFYVTTIPDGFTIESKPSEELLEGQPVLLSCQADSYKYEHLRWYRLNLSTLHDA
HGNPLLLDCKNVHLFATPLAASLEEVAPGARHATLSLSIPRVAPEHEGHYVCEVQDRRSH
DKHCHKKYLSVQALEAPRLTQNLTDLLVNVSDSLEMQCLVAGAHAPSIVWYKDERLLEEK
SGVDLADSNQKLSIQRVREEDAGRYLCSVCNAKGCVNSSASVAVEGSEDKGSMEIVILVG
TGVIAVFFWVLLLLIFCNMRRPAHADIKTGYLSIIMDPGEVPLEEQCEYLSYDASQWEFP
RERLHLGRVLGYGAFGKVVEASAFGIHKGSSCDTVAVKMLKEGATASEHRALMSELKILI
HIGNHLNVVNLLGACTKPQGPLMVIVEFCKYGNLSNFLRAKRDAFSPCAEKSPEQRGRFR
AMVELARLDRRRPGSSDRVLFARFSKTEGGARRASPDQEAEDLWLSPLTMEDLVCYSFQV
ARGMEFLASRKCIHRDLAARNILLSESDVVKICDFGLARDIYKDPDYVRKGSARLPLKWM
APESIFDKVYTTQSDVWSFGVLLWEIFSLGASPYPGVQINEEFCQRLRDGTRMRAPELAT
PAIRRIMLNCWSGDPKARPAFSELVEILGDLLQGRGLQEEEEVCMAPRSSQSSEEGSFSQ
VSTMALHIAQADAEDSPPSLQRHSLAARYYNWVSFPGCLARGAETRGSSRMKTFEEFPMT
PTTYKGSVDNQTDSGMVLASEEFEQIESRHRQESGFSCKGPGQNVAVTRAHPDSQGRRRR
PERGARGGQVFYNSEYGELSEPSEEDHCSPSARVTFFTDNSY

FIG._9

MQRGAALCLRLWLCLGLLDGLVSGYSMTPPTLSITTEESHVIDTGDSLSISCRGQHPLEW
AWPGAQEAPATGDKDSEDTGVVRDCEGTDARPYCKVLLLHEVHANDTGSYVCYYKYIKAR
IEGTTAASIYIFISDTGRPFVEMYSEIPEIIHMTEGRELVIPCRVTSPNITVTLKKFPLD
TLIPDGKRIIWDSRKGFIISNATYKEIGLLTCEATVNGHLYKTNYLTHRTGNELYDIQLL
PRKSLELLVGEKLVLNCTVWAEFNSGVTFDWDYPGKQAERGKWVPERRSQQTHTELSSIL
TIHNVSQHDLGSYVCKANNGIQRFRESTEVRVHENPFISVEWLKGPILEATAGDELVKLP
VKLAAYPPPEFQWYKDGKALSGRHSPHALVLKEVTEASTGTYTLALWNSAAGLRRNISLE
LVVNVPPQIHEKEASSPSIYSRHSRQALTCAYGVPLPLSIQWHWRPWTPCKMFAQRSLR
RRQQQDLMPQCRDWRAVTTQDAVNPIESLDTWTEFVEGKNKTVSKLVIQNANVSAMYKCV
VSNKVGQDERLIYFYVTTIPDGFTIESKPSEELLEGQPVLLSCQADSYKYEHLRWYRLNL
STLHDAHGNPLLLDCKNVHLFATPLAASLEEVAPGARHATLSLSIPRVAPEHEGHYVCEV
QDRRSHDKHCHKKYLSVQALEAPRLTQNLTDLLVNVSDSLEMQCLVAGAHAPSIVWYKDE
RLLEEKSGVDLADSNQKLSIQRVREEDAGRYLCSVCNAKGCVNSSASVAVEGSEDKGSME
IVILVGTGVIAVFFWVLLLLIFCNMRRPAHADIKTGYLSIIMDPGEVPLEEQCEYLSYDA
SQWEFPRERLHLGRVLGYGAFGKVVEASAFGIHKGSSCDTVAVKMLKEGATASEHRALMS
ELKILIHIGNHLNVVNLLGACTKPQGPLMVIVEFCKYGNLSNFLRAKRDAFSPCAEKSPE
QRGRFRAMVELARLDRRRPGSSDRVLFARFSKTEGGARRASPDQEAEDLWLSPLTMEDLV
CYSFQVARGMEFLASRKCIHRDLAARNILLSESDVVKICDFGLARDIYKDPDYVRKGSAR
LPLKWMAPESIFDKVYTTQSDVWSFGVLLWEIFSLGASPYPGVQINEEFCQRLRDGTRMR
APELATPAIRRIMLNCWSGDPKARPAFSELVEILGDLLQGRGLQEEEEVCMAPRSSQSSE
EGSFSQVSTMALHIAQADAEDSPPSLQRHSLAARYYNWVSFPGCLARGAETRGSSRMKTF
EEFPMTPTTYKGSVDNQTDSGMVLASEEFEQIESRHRQESGFSCKGPGQNVAVTRAHPDS
QGRRRRPERGARGGQVFYNSEYGELSEPSEEDHCSPSARVTFFTDNSY

FIG._10

METHODS FOR USING CHIMERIC VASCULAR ENDOTHELIAL GROWTH FACTOR RECEPTOR PROTEINS

CROSS-REFERENCE TO RELATED APPLICATIONS

This application is a continuation of prior application Ser. No. 11/537,623 filed Sep. 30, 2006, which is a continuation of application Ser. No. 11/043,693 filed Jan. 26, 2005, now abandoned which is a continuation of application Ser. No. 10/105,901 filed Mar. 20, 2002, now U.S. Pat. No. 6,897,294, which is a continuation of application Ser. No. 09/348,886 filed Jul. 1, 1999, now U.S. Pat. No. 6,383,486, which is a divisional of application Ser. No. 08/643,839 filed May 7, 1996, now U.S. Pat. No. 6,100,071.

FIELD OF THE INVENTION

The present invention is directed to novel chimeric VEGF receptor proteins comprising amino acid sequences derived from the vascular endothelial growth factor (VEGF) receptors flt-1, KDR and the murine homologue of the human KDR receptor, FLK-1, wherein said chimeric VEGF receptor proteins bind to VEGF and antagonize the endothelial cell proliferative and angiogenic activity thereof. The present invention is also directed to nucleic acids and expression vectors encoding these chimeric VEGF receptor proteins, host cells harboring such expression vectors, pharmaceutically acceptable compositions comprising such proteins, methods of preparing such proteins and to methods utilizing such proteins for the treatment of conditions associated with undesired vascularization.

BACKGROUND OF THE INVENTION

The two major cellular components of the mammalian vascular system are the endothelial and smooth muscle cells. Endothelial cells form the lining of the inner surface of all blood vessels in the mammal and constitute a non-thrombogenic interface between blood and tissue. Therefore, the proliferation of endothelial cells is an important component for the development of new capillaries and blood vessels which, in turn, is a necessary process for the growth and/or regeneration of mammalian tissues.

One protein that has been shown to play an extremely important role in promoting endothelial cell proliferation and angiogenesis is vascular endothelial growth factor (VEGF). VEGF is a heparin-binding endothelial cell growth factor which was originally identified and purified from media conditioned by bovine pituitary follicular or folliculostellate (FS) cells. Ferrara and Henzel, *Biochem. Biophys. Res. Comm.* 161:851-858 (1989). VEGF is a dimer with an apparent molecular mass of about 46 kDa with each subunit having an apparent molecular mass of about 23 kDa. Human VEGF is expressed in a variety of tissues as multiple homodimeric forms (121, 165, 189 and 206 amino acids per monomer), wherein each form arises as a result of alternative splicing of a single RNA transcript. $VEGF_{121}$ is a soluble mitogen that does not bind heparin whereas the longer forms of VEGF bind heparin with progressively higher affinity.

Biochemical analyses have shown that VEGF exhibits a strong mitogenic specificity for vascular endothelial cells. For example, media conditioned by cells transfected with human VEGF cDNA promoted the proliferation of capillary endothelial cells, whereas medium conditioned by control cells did not. Leung, et al., *Science* 246:1306 (1989). Thus, VEGF is known to promote vascular endothelial cell proliferation and angiogenesis, a process which involves the formation of new blood vessels from preexisting endothelium. As such, VEGF may be useful for the therapeutic treatment of numerous conditions in which a growth-promoting activity on the vascular endothelial cells is important, for example, in ulcers, vascular injuries and myocardial infarction.

In contrast, however, while vascular endothelial proliferation is desirable under certain circumstances, vascular endothelial proliferation and angiogenesis are also important components of a variety of diseases and disorders including tumor growth and metastasis, rheumatoid arthritis, psoriasis, atherosclerosis, diabetic retinopathy, retrolental fibroplasia, neovascular glaucoma, age-related macular degeneration, hemangiomas, immune rejection of transplanted corneal tissue and other tissues, and chronic inflammation. Obviously, in individuals suffering from any of these disorders, one would want to inhibit, or at least substantially reduce, the endothelial proliferating activity of the VEGF protein.

In the specific case of tumor cell growth, angiogenesis appears to be crucial for the transition from hyperplasia to neoplasia and for providing nourishment to the growing solid tumor. Folkman, et al., *Nature* 339:58 (1989). Angiogenesis also allows tumors to be in contact with the vascular bed of the host, which may provide a route for metastasis of tumor cells. Evidence for the role of angiogenesis in tumor metastasis is provided, for example, by studies showing a correlation between the number and density of microvessels in histologic sections of invasive human breast carcinoma and actual presence of distant metastasis. Weidner et al., *New Engl. J. Med.* 324:1 (1991). Thus, one possible mechanism for the effective treatment of neoplastic tumors is to inhibit or substantially reduce the endothelial proliferative and angiogenic activity of the VEGF protein.

The endothelial proliferative activity of VEGF is known to be mediated by two high affinity tyrosine kinase receptors, flt-1 and KDR, which exist only on the surface of vascular endothelial cells. DeVries, et al., *Science* 226:989-991 (1992) and Terman, et al., *Oncogene* 6:1677-1683 (1991). Both the flt-1 and KDR tyrosine kinase receptors have seven immunoglobulin-like (Ig-like) domains which form the extracellular ligand-binding regions of the receptors, a transmembrane domain which serves to anchor the receptor on the surface of cells in which it is expressed and an intracellular catalytic tyrosine kinase domain which is interrupted by a "kinase insert". While the KDR receptor binds only the VEGF protein with high affinity, the flt-1 receptor also binds placenta growth factor (PLGF), a molecule having significant structural homology with VEGF. An additional member of the receptor tyrosine kinases having seven Ig-like domains in the extracellular ligand-binding region is FLT4, which is not a receptor for either VEGF or PLGF, but instead binds to a different ligand; VH1.4.5. The VH1.4.5 ligand has been reported in the literature as VEGF-related protein (VRP) or VEGF-C.

Recent gene knockout studies have demonstrated that both the flt-1 and KDR receptors are essential for the normal development of the mammalian vascular system, although their respective roles in endothelial cell proliferation and differentiation appear to be distinct. Thus, the endothelial proliferative and angiogenic activity of the VEGF protein is mediated by binding to the extracellular ligand-binding region of the flt-1 and KDR receptors on the surface of vascular endothelial cells.

In view of the role of VEGF in vascular endothelial proliferation and angiogenesis, and the role that these processes play in many different diseases and disorders, it is desirable to have a means for reducing or inhibiting one or more of the biological activities of VEGF. As such, the present invention is predicated upon research intended to identify the Ig-like domain or domains of the flt-1 and KDR receptor extracellular ligand-binding region which mediate binding to the VEGF protein and inserting or fusing that domain or domains into amino acid sequences derived from another protein to produce a "chimeric VEGF receptor protein". The chimeric VEGF receptor proteins of the present invention will bind to and inactivate endogenous VEGF, thereby providing a means for reducing or inhibiting endogenous VEGF activity and, in turn, reducing or inhibiting endothelial cell proliferation and angiogenesis. Thus, it is an object of the present invention to provide novel chimeric VEGF receptor proteins comprising amino acid sequences derived from the extracellular ligand-binding region of the flt-1 and KDR receptors, wherein said chimeric VEGF receptor proteins are capable of binding to and inhibiting the activity of VEGF.

Further objects of the present invention are to provide nucleic acids encoding chimeric VEGF receptor proteins of the present invention, replicable expression vectors capable of expressing such chimeric proteins, host cells transfected with those expression vectors, pharmaceutical compositions comprising the chimeric VEGF receptor proteins of the present invention, methods for preparing such chimeric proteins and method of using those chimeric proteins for the therapeutic treatment of an individual in need thereof.

SUMMARY OF THE INVENTION

The objects of this invention, as generally defined supra, are achieved by the provision of chimeric VEGF receptor proteins which are capable of binding to VEGF and exerting an inhibitory effect thereon, wherein said chimeric VEGF receptor protein comprises Ig-like domains 1, 2 and 3 of the flt-1 and/or the KDR receptor (or the murine homologue of the KDR receptor, FLK-1) or functional equivalents thereof.

In a preferred embodiment, the chimeric VEGF receptor proteins of the present invention contain flt-1 or KDR receptor amino acid sequences corresponding only to Ig-like domains 1, 2 and 3 of the extracellular ligand-binding region thereof and each Ig-like domain is derived from the same VEGF receptor.

In other embodiments, however, the chimeric VEGF receptor proteins of the present invention comprise Ig-like domains 1, 2 and 3 of the extracellular ligand-binding region of the flt-1 or KDR receptor in addition to one or more of the remaining four immunoglobulin-like domains thereof. Preferably, the Ig-like domains employed are derived from the same receptor, however, a combination of Ig-like domains derived from both the flt-1 and KDR receptors will find use.

In another embodiment of the present invention, the chimeric VEGF receptor proteins of the present invention comprise the extracellular ligand-binding region of the FLT4 receptor wherein at least Ig-like domain 2 of the FLT4 receptor is replaced with the Ig-like domain 2 of either the flt-1 or KDR receptor. Preferably, only Ig-like domain 2 of the FLT4 receptor is replaced by the corresponding Ig-like domain from either the flt-1 or KDR receptor, however, other domains may also be similarly replaced.

A further aspect of the present invention is directed to nucleic acid sequences encoding the chimeric VEGF receptor proteins described herein and functional equivalents thereof. It is well known to the ordinarily skilled artisan that such nucleic acids can vary due to the degeneracy of the genetic code and such nucleic acid variants are also encompassed by the present invention.

In still other embodiments, the present invention relates to replicable expression vectors encoding the various chimeric VEGF receptor proteins described supra, host cells transfected with those expression vectors and compositions comprising the chimeric VEGF receptor proteins described supra compounded with a pharmaceutically acceptable excipient.

In yet other embodiments, the present invention relates to methods for producing the chimeric VEGF receptor proteins described supra by introducing an expression vector encoding the desired chimeric protein into an appropriate expression systems and effecting the expression of said protein.

Yet another aspect of the invention provides for the use of the chimeric VEGF receptor proteins of the present invention for the treatment of conditions associated with inappropriate vascularization wherein an inhibition of vascularization and angiogenesis is desirable.

BRIEF DESCRIPTION OF THE DRAWINGS

FIGS. 1A and 1B shows an alignment of the amino acid sequences for the extracellular ligand-binding regions of the flt-1, (SEQ ID NO:1), KDR (SEQ ID NO:2), and FLT4 (SEQ ID NO:3), receptors. Amino acids are presented by their standard single letter designations. Dashes are inserted to create the best fit for alignment of the seven Ig-like domains. The seven Ig-like domains of each extracellular ligand-binding region of each receptor presented are shown as boxed areas.

FIG. 2 presents the oligonucleotides (SEQ ID NOs. 4, 6, 8, 10, 12, 14, 16, 18, 20, 22, 24, 26, 28, and 30 used in the oligonucleotide-directed mutagenesis-generated deletions of each of the seven Ig-like domains existing within the extracellular ligand-binding region of the flt-1 receptor. The restriction sites created in the DNA sequence are underlined and are listed above the underlined sequence. Amino acids are presented by their standard one-letter designations (SEQ ID Nos: 5, 7, 9, 11, 13, 15, 17, 19, 21, 23, 25, 27, 29, and 31). Numbers shown in parentheses designate the amino acid number. In some cases, amino acids were changed when the restriction sites were designed into the oligonucleotides. These amino acid changes are underlined and the original amino acid at that position is presented below in parentheses.

FIG. 3 shows the ability of intact flt-1/IgG chimeric VEGF receptor protein and various flt-1/IgG domain deletion chimeric proteins to specifically bind to the VEGF ligand. Binding efficiency is presented as the total cpm bound per 5 ng of immunoreactive (ir) $F_c$. "wt" refers to the intact flt-1/IgG chimeric VEGF receptor protein. "d1" through "d7" refer to the flt-1/IgG domain deletion chimeras where the number corresponds to the Ig-like domain that is deleted.

FIG. 4 shows the ability of intact flt-1/IgG chimeric VEGF receptor protein and various flt-1/IgG domain deletion chimeric proteins to specifically bind to the VEGF ligand. Binding efficiency is presented as the total cpm bound per 4.5 ng of immunoreactive (ir) $F_c$. "flt-wt" refers to the intact flt-1/IgG chimeric protein. "flt(1,2)" is the chimeric protein having only flt-1 Ig-like domains 1 and 2 fused to the $F_c$ of IgG. "flt(2)" is the chimeric protein having only flt-1 Ig-like domain 2 fused to the $F_c$ of IgG. "flt(2,3)" is the chimeric protein having only flt-1 Ig-like domains 2 and 3 fused to the $F_c$ of IgG. "flt(1,2,3)" is the chimeric protein having only flt-1 Ig-like domains 1, 2 and 3 fused to the $F_c$ of IgG. Finally, "KDR(2)" is a chimeric VEGF receptor protein wherein only the Ig-like domain 2 of the extracellular ligand-binding region of the KDR receptor is fused to the $F_c$ of IgG.

FIG. 5 shows the percent binding of the VEGF ligand to the intact flt-1/IgG chimeric VEGF receptor protein and to the flt(1,2,3) deletion chimera in the presence of increasing amounts of unlabeled VEGF competitor. "●" designates binding by the flt(1,2,3) deletion chimera. "♦" designates binding by the intact flt-1/IgG chimeric protein.

FIG. 6 shows the ability of intact flt-1/IgG chimeric VEGF receptor protein and various Ig-like domain 2 "swap" mutants to specifically bind to the VEGF ligand. Binding efficiency is presented as the total cpm bound per 1 ng of immunoreactive (ir) $F_c$. "flt-1" refers to the native flt-1/IgG chimeric protein. "flt.d2" refers to the flt-1/IgG chimeric protein having a deletion of Ig-like domain 2. "flt.K2" refers to the "swap" chimera protein where the Ig-like domain 2 of the flt-1/IgG protein is replaced with the Ig-like domain 2 of the KDR receptor. Finally, "fltF4.2" refers to the "swap" chimera protein where the Ig-like domain 2 of the flt-1 protein is replaced with the Ig-like domain 2 of the FLT4 receptor.

FIG. 7 shows the percent inhibition of VEGF binding by either unlabeled VEGF competitor or unlabeled PLGF competitor with various flt-1/IgG "swap" chimeric proteins. "flt" and "KDR" designate the native flt-1 and native KDR receptor, respectively. "flt.K1" refers to the "swap" chimera wherein the Ig-like domain 1 of the flt-1 receptor is replaced by the Ig-like domain 1 of the KDR receptor. "flt.K2" refers to the "swap" chimera wherein the Ig-like domain 2 of the flt-1 receptor (SEQ ID NO:49) is replaced by the Ig-like domain 2 of the KDR receptor (SEQ ID NO:50). "flt.K3" refers to the "swap" chimera wherein the Ig-like domain 3 of the flt-1 receptor (SEQ ID NO:51) is replaced by the Ig-like domain 3 of the KDR receptor (SEQ ID NO:52). "flt.K5" refers to the "swap" chimera wherein the Ig-like domain 5 of the flt-1 receptor is replaced by the Ig-like domain 5 of the KDR receptor. Finally, "flt.K7" refers to the "swap" chimera wherein the Ig-like domain 7 of the flt-1 receptor is replaced by the Ig-like domain 7 of the KDR receptor.

FIG. 8 shows the entire amino acid sequence (SEQ ID NO:32) of the intact FLT4 receptor. Amino acid residues are presented in their standard one-letter designations.

FIG. 9 shows the entire amino acid sequence (SEQ ID NO:33) of the receptor encoded by the flt-1(1,2,3)/FLT4 expression construct. Underlined amino acid residues are those derived from Ig-like domains 1-3 of the flt-1 receptor and which replace the Ig-like domains 1-3 of the FLT4 receptor. The bolded amino acid residue differs from the wild type FLT4 amino acid residue normally at that position. Amino acid residues are presented in their standard one-letter designations.

FIG. 10 shows the entire amino acid sequence (SEQ ID NO:34) of the receptor encoded by the flt-1 (2)/FLT4 expression construct. Underlined amino acid residues are those derived from Ig-like domain 2 of the flt-1 receptor and which replace the Ig-like domain 2 of the FLT4 receptor. The bolded amino acid residues differ from the wild type FLT4 amino acid residues normally at that position. Amino acid residues are presented in their standard one-letter designations.

DETAILED DESCRIPTION OF THE INVENTION

A. Definitions

As used herein, the term "chimeric VEGF receptor protein" means a receptor molecule having amino acid sequences derived from at least two different proteins, at least one of which is the flt-1 or KDR receptor, said receptor molecule being capable of binding to and inhibiting the activity of VEGF. Preferably, the chimeric VEGF receptor proteins of the present invention consist of amino acid sequences derived from only two different VEGF receptor molecules, however, amino acid sequences comprising Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art.

The term "KDR receptor" as used herein is meant to encompass not only the KDR receptor but also the murine homologue of the human KDR receptor, designated FLK-1.

"Immunoglobulin-like domain" or "Ig-like domain" refers to each of the seven independent and distinct domains that are found in the extracellular ligand-binding region of the flt-1, KDR and FLT4 receptors. Ig-like domains are generally referred to by number, the number designating the specific domain as it is shown in FIGS. 1A and 1B. As used herein, the term "Ig-like domain" is intended to encompass not only the complete wild-type domain, but also insertional, deletional and substitutional variants thereof which substantially retain the functional characteristics of the intact domain. It will be readily apparent to those of ordinary skill in the art that numerous variants of the Ig-like domains of the flt-1 and KDR receptors can be obtained which will retain substantially the same functional characteristics as the wild type domain.

"Soluble" as used herein with reference to the chimeric VEGF receptor proteins of the present invention is intended to mean chimeric VEGF receptor proteins which are not fixed to the surface of cells via a transmembrane domain. As such, soluble forms of the chimeric VEGF binding proteins of the present invention, while capable of binding to and inactivating VEGF, do not comprise a transmembrane domain and thus generally do not become associated with the cell membrane of cells in which the molecule is expressed. A soluble form of the receptor exerts an inhibitory effect on the biological activity of the VEGF protein by binding to VEGF, thereby preventing it from binding to its natural receptors present on the surface of target cells.

"Membrane-bound" as used herein with reference to the chimeric VEGF receptor proteins of the present invention is intended to mean chimeric VEGF receptor proteins which are fixed, via a transmembrane domain, to the surface of cells in which they are expressed.

"Functional equivalents" when used in reference to the Ig-like domains of the extracellular ligand-binding regions of the flt-1, KDR or FLT4 receptors means the Ig-like domain or domains possess at least one particular alteration, such as a deletion, addition and/or substitution therein yet retains substantially the same functional characteristics as does the wild type Ig-like domain or domains with reference more specifically to Ig-like domains 1, 2 and 3 of the flt-1 and/or KDR receptor, "functional equivalents" intends scope of so much of such domains as to result in at least substantial binding to VEGF, i.e., a partial sequence of each of said domains that will produce a binding effect.

"Inhibitory effect" when used in reference to the activity of a chimeric VEGF receptor protein of the present invention means that the chimeric VEGF receptor protein binds to and substantially inhibits the activity of VEGF. Generally, the result of this Inhibitory effect is a decrease in the vascularization and/or angiogenesis which occurs as a result of the VEGF protein.

"Undesired vascularization" refers to the endothelial proliferation and/or angiogenesis which is associated with an undesirable disease or disorder and which, if reduced or eliminated, would result in a reduction or elimination of the undesirable characteristics of the disease or disorder. For example, the vascularization and/or angiogenesis associated with tumor formation and metastasis and various retinopathies is undesirable.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N., *Proc. Natl. Acad. Sci.* (*USA*), 69, 2110 (1972) and Mandel et al. *J. Mol. Biol.* 53, 164 (1970), is generally used for prokaryotes or other cells that contain substantial cell-wall barriers. For mammalian cells without such cell walls, the calcium phosphate precipitation method of Graham, F. and van der Eb, A., *Virology*, 52, 456-457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. *J. Bact.*, 130, 946 (1977) and Hsiao, C. L., et al. *Proc. Ned. Acad. Sci.* (*USA*) 76, 3829 (1979). However, other methods for introducing DNA into cells such as by nuclear injection, electroporation or by protoplast fusion may also be used.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 mg of plasmid or DNA fragment is used with about 1-2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al. 1982, *Molecular Cloning: A Laboratory Manual* (New York: Cold Spring Harbor Laboratory, 1982) pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9, 6103-8114 (1981) and D. Goeddel et al., *Nucleic Acids Res.* 8, 4057 (1980).

"Ligation" refers to the process of forming phosphodiester bonds between two double stranded nucleic acid fragments (T. Maniatis et al. 1982, supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis at al. 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.* 14, 5399-5407 [1986]). They are then purified on polyacrylamide gels.

B. General Methodology

1. Amino Acid Sequence Variants

It will be appreciated that various amino acid substitutions can be made in the Ig-like domain or domains of the chimeric VEGF receptor proteins of the present invention without departing from the spirit of the present invention with respect to the chimeric proteins' ability to bind to and inhibit the activity of VEGF. Thus, point mutational and other broader variations may be made in the Ig-like domain or domains of the chimeric VEGF receptor proteins of the present invention so as to impart interesting properties that do not substantially effect the chimeric protein's ability to bind to and inhibit the activity of VEGF. These variants may be made by means generally known well in the art.

a. Covalent Modifications

Covalent modifications may be made to various amino acid residues of the Ig-like domain or domains present in the chimeric VEGF receptor protein, thereby imparting new properties to that Ig-like domain or domains without eliminating the capability to bind to and inactivate VEGF.

For example, cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the chimeric VEGF receptor protein to a water-insoluble support matrix or surface for use in the method for purifying the VEGF protein from complex mixtures. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties*, W.H. Freeman & Co., San Francisco, pp. 79-86 [1983]), acetylation of the N-terminal amine, and, in some instances, amidation of the C-terminal carboxyl group.

b. DNA Mutations

Amino acid sequence variants of the Ig-like domain or domains present in the chimeric VEGF receptor proteins of the present invention can also be prepared by creating mutations in the DNA encoding the chimeric protein. Such variants include, for example, deletions from, or insertions or substitutions of, amino acid residues within the amino acid sequence of the Ig-like domain or domains. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, variants of the Ig-like domain or domains present in the chimeric VEGF receptor proteins of the present invention ordinarily are prepared by site-directed mutagenesis of nucleotides in the DNA encoding the Ig-like domain or domains, thereby producing DNA encoding the variant, and thereafter expressing the DNA in recombinant cell culture. The variants typically exhibit the same qualitative ability to bind to the VEGF ligand as does the unaltered chimeric protein.

While the site for introducing an amino acid sequence variation in the Ig-like domain or domains of the chimeric VEGF receptor protein is predetermined, the mutation per se need not be predetermined. For example, to optimize the performance of a mutation at a given site, random mutagenesis may be conducted at the target codon or region and the expressed chimeric protein variants screened for the optimal combination of desired attributes such as ability to specifically bind to the VEGF ligand, in vivo half-life, and the like. Techniques for making substitution mutations at predetermined sites in DNA having a known sequence are well known, for example, site-specific mutagenesis.

Preparation of variants in the Ig-like domain or domains of a chimeric VEGF receptor protein in accordance herewith is preferably achieved by site-specific mutagenesis of DNA that encodes an earlier prepared chimeric protein. Site-specific mutagenesis allows the production of Ig-like domain variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2, 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153, 3 [1987]) may be employed to obtain single-stranded DNA.

In general, site-directed mutagenesis in accordance herewith is performed by; first obtaining a single-stranded vector that includes within its sequence a DNA sequence that encodes the relevant chimeric VEGF receptor protein. An oligonucleotide primer bearing the desired mutated sequence is prepared, generally synthetically, for example, by the method of Crea et al., *Proc. Natl. Acad. Sci. (USA)*, 75, 5765 (1978). This primer is then annealed with the single-stranded chimeric protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated DNA encoding the variant chimeric VEGF receptor protein may be removed and placed in an appropriate vector for protein production, generally an expression vector of the type that may be employed for transformation of an appropriate host.

c. Types of Mutations

Amino acid sequence deletions generally range from about 1 to 15 residues, more preferably 1 to 7 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the Ig-like domain sequences) may range generally from about 1 to 10 residues, more preferably 1 to 5. An example of a terminal insertion includes a fusion of a signal sequence, whether heterologous or homologous to the host cell, to the N-terminus of the chimeric VEGF receptor protein to facilitate the secretion of the chimeric protein from recombinant hosts.

The third group of mutations which can be introduced into the Ig-like domain or domains present in the chimeric VEGF receptor protein are those in which at least one amino acid residue in the Ig-like domain or domains, and preferably only one, has been removed and a different residue inserted in its place. Such substitutions preferably are made in accordance with the following Table 1 when it is desired to modulate finely the characteristics of the Ig-like domain or domains.

TABLE 1

| Original Residue | Exemplary Substitutions |
| --- | --- |
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| The (T) | ser |
| Trp (W) | tyr |
| Tyr (Y) | trp; phe |
| Val (V) | ile; leu |

Substantial changes in function or immunological identity are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in the properties of the Ig-like domains will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (a) a residue having an electronegative side chain is substituted for (or by) a residue having an electropositive charge; or (f) a residue having a bulky side chain, e.g., phenylalanine, is substituted for (or by) one not having such a side chain, e.g., glycine.

Most deletions and insertions, and substitutions in particular, are not expected to produce radical changes in the characteristics of the Ig-like domain or domains of the chimeric VEGF receptor protein. However, when it is difficult to predict the exact effect of the substitution, deletion, or insertion in advance of doing so, one skilled in the art will appreciate that the effect will be evaluated by routine screening assays. For example, an Ig-like domain variant typically is made by site-specific mutagenesis of the nucleic acid encoding the intact chimeric VEGF receptor protein, expression of the variant nucleic acid in recombinant cell culture, purification of the variant chimeric VEGF receptor protein from the cell culture and detecting the ability of the variant chimeric VEGF receptor protein to specifically bind to a VEGF ligand. Binding assays which can be routinely employed to determine if a particular alteration or alterations in an Ig-like domain or domains affects the capability of the chimeric VEGF receptor protein to bind to and inhibit the activity of VEGF are described both in the Examples below and in the article by Park et al., *J. Biol. Chem.* 269:25646-25654 (1994) which is expressly incorporated by reference herein.

Thus, the activity of a variant chimeric VEGF receptor protein may be screened in a suitable screening assay for the desired characteristic. For example, a change in the ability to specifically bind to a VEGF ligand can be measured by a competitive-type VEGF binding assay. Modifications of such protein properties as redox or thermal stability, hydrophobicity, susceptibility to proteolytic degradation, or the tendency to aggregate with carriers or into multimers are assayed by methods well known to the ordinarily skilled artisan.

2. Recombinant Expression

The chimeric VEGF receptor proteins of the present invention are prepared by any technique, including by well known recombinant methods. Likewise, an isolated DNA is understood herein to mean chemically synthesized DNA, cDNA, chromosomal, or extrachromosomal DNA with or without the 3'- and/or 5'-flanking regions. Preferably, the desired chimeric VEGF receptor protein herein is made by synthesis in recombinant cell culture.

For such synthesis, it is first necessary to secure nucleic acid that encodes a chimeric VEGF receptor protein of the present invention. DNA encoding a flt-1 or KDR receptor may be obtained from vascular endothelial cells by (a) preparing a cDNA library from these cells, (b) conducting hybridization analysis with labeled DNA encoding the flt-1 or KDR receptor or fragments thereof (up to or more than 100 base pairs in length) to detect clones in the library containing homologous sequences, and (c) analyzing the clones by restriction enzyme analysis and nucleic acid sequencing to identify full-length clones. If full-length clones are not present in a cDNA library, then appropriate fragments may be recovered from the various clones using the nucleic acid and amino acid sequence information known for the flt-1 and KDR receptors and ligated at restriction sites common to the clones to assemble a full-length clone encoding the flt-1 or KDR domain. Alternatively, genomic libraries may provide the desired DNA.

Once this DNA has been identified and Isolated from the library, this DNA may be ligated into an appropriate expression vector operably connected to appropriate control sequences. Moreover, once cloned into an appropriate vector, the DNA can be altered in numerous ways as described above to produce functionally equivalent variants thereof. Additionally, DNA encoding various domains, such as the intracellular, transmembrane and/or various Ig-like domains can be deleted and/or replaced by DNA encoding corresponding domains from other receptors. DNA encoding unrelated amino acid sequences, such as the $F_c$ portion of an immunoglobulin molecule, may also be fused to the DNA encoding some or all of the VEGF receptor, thereby producing a chimeric VEGF receptor molecule.

In one example of a recombinant expression system, an Ig-like domain containing chimeric VEGF receptor protein is expressed in mammalian cells by transformation with an expression vector comprising DNA encoding the chimeric VEGF receptor protein. It is preferable to transform host cells capable of accomplishing such processing so as to obtain the chimeric protein in the culture medium or periplasm of the host cell, i.e., obtain a secreted molecule.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention.

For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2, 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., *Nature,* 375, 615 [1978]; Itakura et al., *Science,* 198, 1056 [1977]; Goeddel et al., *Nature,* 281, 544 [1979]) and a tryptophan (trp) promoter system (Goeddel et al., *Nucleic Acids Res.,* 8, 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell,* 20, 269 [1980]).

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. For expression in *Saccharomyces,* the plasmid YRp7, for example (Stinchcomb et al., *Nature* 282, 39 [1979]; Kingsman et al., *Gene* 7, 141 [1979]; Tschemper et al., *Gene.* 10, 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85, 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 [1980]) or other glycolytic enzymes (Hess et al., *J. Adv. Enzyme Reg.* 7, 149 [1968]; Holland et al., *Biochemistry* 17, 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture,* Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication [Fiers et al., *Nature,* 273, 113 (1978)]. Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both chimeric protein and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Aced. Sci.* (*USA*) 77, 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.* 8, 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.* 9, 309 (1981) or by the method of Maxam et al., *Methods of Enzymology* 65, 499 (1980).

After introduction of the DNA into the mammalian cell host and selection in medium for stable transfectants, amplification of DHFR-protein-coding sequences is effected by growing host cell cultures in the presence of approximately 20,000-500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in the Examples.

c. VEGF Receptor-Immunoglobulin Chimeras (Immunoadhesins)

Immunoglobulins and certain variants thereof are known and may have been prepared in recombinant cell culture. For example, see U.S. Pat. No. 4,745,055; EP 256,654; Faulkner et al., *Nature* 298:286 (1982), EP 120,694, EP 125,023, Morrison, *J. Immunol.* 123:793 [1979]); Kohler et al., *Proc. Natl. Aced. Sci. USA* 77:2197 (1980); Raso et al., *Cancer Res.* 41:2073 (1981); Morrison, *Ann. Rev. Immunol.* 2:239 (1984); Morrison, *Science* 229:1202 (1985); Morrison et al., *Proc. Natl. Aced. Sci. USA* 81:6851 (1984); EP 255,694, EP 266, 663; and WO 88/03559. Reassorted immunoglobulin chains are also known. See, for example, U.S. Pat. No. 4,444,878; WO 88/03565; and EP 68,763 and references cited therein.

Chimeras constructed from a protein receptor sequence linked to an appropriate immunoglobulin constant domain sequence (immunoadhesins) are known in the art. Immunoadhesins reported in the literature include fusions of the T cell receptor (Gascoigne et al., *Proc. Natl. Aced. Sci. USA* 84:2936-2940 [1987]), CD4 (Capon et al., *Nature* 337:525-531 [1989]), L-selectin (homing receptor) (Watson et al., *J. Cell. Biol.* 110:2221-2229 [1990]), CD44 (Aruffo et al., *Cell* 61: 1303-1313 [1990]), CD28 and B7 (Linsley at al., *J. Exp. Med.* 173:721-730 [1991]), CTLA-4 (Linsley et al., *J. Exp. Med.* 174:561-569 [1991]), CD22 (Stamenkovic et al., *Cell* 66:1133-1144 [1991]), TNF receptor (Ashkenazi at al., *Proc. Natl. Acad. Sci. USA* 88:10535-10539 [1991]) and IgE receptor alpha (Ridgway et al., *J. Cell. Biol.* 115:abstr. 1448 [1991]).

The simplest and most straightforward immunoadhesin design combined the binding region(s) of an "adhesin" protein with the Fc regions of an immunoglobulin heavy chain. Ordinarily, when preparing the chimeric VEGF receptors of the present invention having immunoglobulin sequences, nucleic acid encoding the Ig-like domains of the VEGF receptor(s) will be fused C-terminally to nucleic acid encoding the N-terminus of an immunoglobulin constant domain sequence, however, N-terminal fusions are also possible.

Typically, in such fusions, the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the VEGF receptor/immunoglobulin chimera.

In some embodiments, the VEGF receptor/Ig chimeras of the present invention may be assembled as monomers, or hetero- or homo-multimers, and particularly as dimers and trimers, essentially as illustrated in WO 91/08298.

In a preferred embodiment, the VEGF receptor Ig-like domains of interest are fused to the N-terminus of the Fc domain of immunoglobulin $G_1$ (IgG-1). It is possible to fuse the entire heavy chain constant region to the VEGF receptor Ig-like domains of interest. However, more preferably, a sequence beginning in the hinge region just upstream of the papain cleavage site which defines Fc chemically, or analogous sites of other immunoglobulins are used in the fusion. In a particularly preferred embodiment, the Ig-like domains of the VEGF receptor of interest are fused to (a) the hinge region and CH2 and CH3 or (b) the CH1, hinge, CH2 and CH3 domains, of an IgG-1, IgG-2 or IgG-3 heavy chain. The precise site at which the fusion is made is not critical, and the optimal site can be determined by routine experimentation.

In some embodiments, the Ig-like domains VEGF receptor/immunoglobulin chimeras of the present invention are assembled as multimers, and particularly as homo-dimers or -tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum.

Ig-like domain sequences from the VEGF receptors can also be inserted between immunoglobulin heavy and light chain sequences, such that an immunoglobulin comprising a chimeric heavy chain is obtained. In this embodiment, the VEGF receptor Ig-like sequences are fused to the 3' end of an immunoglobulin heavy chain in each are of the immunoglobulin, either between the hinge and the CH2 domain, or between the CH2 and CH3 domains. Similar constructs have been reported by Hoogenboom, et al. *Mol. Immunol.* 28:1027-1037 (1991).

Although the presence of an immunoglobulin light chain is not required in the immunoadhesins of the present invention, an immunoglobulin light chain might be present either covalently associated to a VEGF receptor Ig-like domain-immunoglobulin heavy chain fusion polypeptide, or directly fused to the VEGF receptor Ig-like domains. In the former case, DNA encoding an immunoglobulin light chain is typically coexpressed with the VEGF receptor Ig-like domain-immunoglobulin heavy chain chimeric protein. Upon secretion, the hybrid heavy chain and light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816, 567, issued 28 Mar. 1989.

In a preferred embodiment, the immunoglobulin sequences used in the construction of the immunoadhesins of the present invention are from an IgG immunoglobulin heavy chain domain. For human immunoadhesins, the use of human IgG1 and IgG3 immunoglobulin sequences is preferred. A major advantage of using the IgG1 is that IgG1 immunoadhesins can be purified efficiently on immobilized protein A. However, other structural and functional properties should be taken into account when choosing the Ig fusion partner for a particular immunoadhesin construction. For example, the IgG3 hinge is longer and more flexible, so that it can accommodate larger "adhesin" domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For VEGF receptor Ig-like domain/immunoglobulin chimeras designed for in vivo applications, the pharmacokinetic properties and the effector functions specified by the Fc region are important as well. Although IgG1, IgG2 and IgG4 all have in vivo half-lives of 21 days, their relative potencies at activating the complement system are different. Moreover, various immunoglobulins possess varying numbers of allotypic isotypes.

The general methods suitable for the construction and expression of immunoadhesins are the same as those described herein above with regard to (native or variant) Ig-like domains of the various VEGF receptors. Chimeric immunoadhesins of the present invention are most conveniently constructed by fusing the cDNA sequence encoding the VEGF receptor Ig-like domain(s) of interest in-frame to an Ig cDNA sequence. However, fusion to genomic Ig fragments can also be used (see, e.g., Gascoigne et al., supra). The latter type of fusion requires the presence of Ig regulatory sequences for expression. cDNAs encoding IgG heavy chain constant regions can be isolated based on published sequences from cDNA libraries derived from spleen or peripheral blood lymphocytes, by hybridization or by polymerase chain reaction (PCR) techniques. The cDNAs encoding the "adhesin" derived from the VEGF receptor Ig-like domain(s) and the Ig parts of the chimera are inserted in tandem into a plasmid vector that directs efficient expression in the chosen host cells. The exact junction can be created by removing the extra sequences between the designed junction codons using oligonucleotide-directed deletional mutagenesis (Zoller and Smith, *Nucl. Acids Res.* 10:6487 (1982)). Synthetic oligonucleotides can be used, in which each half is complementary to the sequence on either side of the desired junction. Alternatively, PCR techniques can be used to join the two parts of the molecule in-frame with an appropriate vector.

The chimeric immunoadhesins of the present invention can be purified by various well known methods including affinity chromatography on protein A or G, thiophilic gel chromatography (Hutchens et al., *Anal. Biochem.* 159:217-226 [1986]) and immobilized metal chelate chromatography (Al-Mashikhi et al., *J. Dairy Sci.* 71:1756-1763 [1988]).

d. Therapeutic Uses and Formulations

For therapeutic applications, the chimeric VEGF receptor proteins of the present invention are administered to a mammal, preferably a human, in a pharmaceutically acceptable dosage form, including those that may be administered to a human intervenously as a bolus or by continuous infusion over a period of time, by intramuscular, intraperitoneal, intracerebrospinal, subcutaneous, intra-arterial, intrasynovial, intrathecal, oral, topical, or inhalation routes. The chimeric VEGF receptor proteins of the present invention are also suitably administered by intratumoral, peritumoral, intralesional or perilesional routes, to exert local as well as systemic effects. The intraperitoneal route is expected to be particularly useful, for example, in the treatment of ovarian tumors.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of chimeric protein include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nanocapsules, liposomes, plasters, inhalation forms, nose sprays, sublingual tablets, and sustained release preparations. For examples of sustained release compositions, see U.S. Pat. No. 3,773,919, EP 58,481A, U.S. Pat. No. 3,887,699, EP 158, 277A, Canadian Patent No. 1176565, U. Sidman et al., *Biopolymers* 22:547 (1983) and R. Langer et al., *Chem. Tech.* 12:98 (1982). The chimeric protein will usually be formulated in such vehicles at a concentration of about 0.1 mg/ml to 100 mg/ml.

Optionally other ingredients may be added to pharmaceutical formulations of the chimeric VEGF receptor proteins of the present invention such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The chimeric VEGF receptor protein formulation to be used for therapeutic administration must be sterile. Sterility is readily accomplished by filtration through sterile filtration membranes (e.g., 0.2 micron membranes). The chimeric VEGF receptor protein ordinarily will be stored in lyophilized form or as an aqueous solution if it is highly stable to thermal and oxidative denaturation. The pH of the chimeric VEGF receptor protein preparations typically will be about from 6 to 8, although higher or lower pH values may also be appropriate in certain instances.

For the prevention or treatment of disease, the appropriate dosage of chimeric VEGF receptor protein will depend upon the type of disease to be treated, the severity and course of the disease, whether the chimeric VEGF receptor proteins are administered for preventative or therapeutic purposes, previous therapy, the patient's clinical history and response to the chimeric VEGF receptor protein and the discretion of the attending physician. The chimeric VEGF receptor protein is suitable administered to the patient at one time or over a series of treatments. For purposes herein, the "therapeutically effective amount" of a chimeric VEGF receptor protein is an amount that is effective to either prevent, lessen the worsening of, alleviate, or cure the treated condition, in particular that amount which is sufficient to reduce or inhibit the proliferation of vascular endothelium in vivo.

The chimeric VEGF receptor proteins of the present invention are useful in the treatment of various neoplastic and non-neoplastic diseases and disorders. Neoplasms and related conditions that are amenable to treatment include carcinomas of the breast, lung, esophagus, gastric anatomy, colon, rectum, liver, ovary, cervix, endometrium, thecomas, arrhenoblastomas, endometrial hyperplasia, endometriosis, fibrosarcomas, choriocarcinoma, head and neck cancer, nasopharyngeal carcinoma, laryngeal carcinoma, hepatoblastoma, Karposi's sarcoma, melanoma, skin carcinomas, hemangioma, cavernous hemangioma; hemangioblastoma, pancreas carcinoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as associated with brain tumors), and Meigs' syndrome.

Non-neoplastic conditions that are amenable to treatment include rheumatoid arthritis, psoriasis, atherosclerosis, diabetic and other retinopathies, retrolental fibroplasia, neovascular glaucoma, age-related macular degeneration, thyroid hyperplasias (including grave's disease), corneal and other tissue transplantation, chronic inflammation, lung inflammation, nephrotic syndrome, preclampasia, ascites, pericardial effusion (such as associated with pericarditis) and pleural effusion.

The following examples are intended merely to illustrate the best mode now known for practicing the invention but the invention is not to be considered as limited to the details of such examples.

EXAMPLE 1

Construction and Analysis of the flt-1 Extracellular Domain/IgG $F_c$ Chimera (flt-1/IgG) and Deletion Constructs Thereof An expression construct consisting of the native flt-1 extracellular ligand-binding region, having seven Ig-like domains, fused to the $F_c$ portion of human IgG, was constructed essentially as described by Park at al., *J. Biol. Chem.* 269:25646-25654 (1994) which is expressly incorporated herein by reference. Specifically, the extracellular ligand-binding region of the flt-1 receptor was cloned by the polymerase chain reaction using Pfu polymerase. Human placental cDNA served as the template. Primers encompassed the entire extracellular ligand-binding region of the cDNA encoding the flt-1 extracellular ligand-binding region, including signal peptides. Shibuya at al., *Oncogene* 5:519-524 (1990) and deVries at al., *Science* 255:989-991 (1992). The cDNA for the flt-1 extracellular ligand-binding region was cloned in two pieces to facilitate sequencing. Two sets of primers (shown below) were used, and the resulting band (approximately 1 kilobase in size) was digested with the appropriate enzymes and subcloned into pBluescript II or pSL301. The cDNA produced encoded the first 758 amino acids of the flt-1 receptor. Full-length flt-1 extracellular ligand-binding region cDNA was created by ligating the two flt-1 polymerase chain reaction clones at a unique natural Mun I restriction site.

```
flt-1 primer set #1:
5' TCTAGAGAATTCCATGGTCAGCTACTGGGACACC 3'
(SEQ ID NO: 35)

5' CCAGGTCATTTGAACTCTCGTGTTC 3'
(SEQ ID NO: 36)

flt-1 primer set #2:
5' TACTTAGAGGCCATACTCTTGTCCT 3'
(SEQ ID NO: 37)

5' GGATCCTTCGAAATTAGACTTGTCCGAGGTTC 3'
(SEQ ID NO: 38)
```

These primers changed amino acid 757 of the flt-1 extracellular ligand-binding region to phenylalanine and introduced a Bst BI site at the 3' end thereof. A Bst BI mutation which eliminated any linker sequences was introduced at the 5' end of $CH_2CH_3$, an IgGγ1 heavy chain cDNA clone. Capon, et al., *Nature* 337:525-531 (1989). The flt-1 extracellular ligand-binding region sequences were then fused to the coding sequences for amino acids 216-443 of this IgGγ1 heavy chain clone via the unique Bst BI site at the 3' end of the flt-1 extracellular ligand-binding region coding region. This construct was then subcloned into the plasmid pHEBO23 for expression in CEN4 cells as described by Park at al., *Mol. Biol. Cell.* 4:1317-1326 (1993). The authenticity of the clone was verified by DNA sequencing. This resulted in the successful construction of the chimera "flt-1/IgG" wherein the native extracellular ligand-binding region of the flt-1 receptor is fused to the $F_c$ portion of human IgG.

The amino acid sequences of the extracellular ligand-binding region of the flt-1, KDR and FLT4 receptors were then aligned using the sequence analysis program "align" and the boundaries of each of the seven Ig-like domains present in the extracellular ligand-binding regions of the flt-1, KDR and FLT4 receptors were determined by structural and sequence considerations. FIGS. 1A and 1B present the alignment of the extracellular ligand-binding regions of the flt-1, KDR and FLT4 receptors.

Once the boundaries of the seven Ig-like domains in the extracellular ligand-binding regions of the flt-1, KDR and FLT4 receptors were defined as shown in FIGS. 1A and 1B, the flt-1/IgG construct prepared above was utilized as a template to systematically delete each of the seven individual Ig-like domains of the flt-1 extracellular ligand-binding region by employing the "loop-out" mutagenesis technique previously described by Urfer et al., *EMBO J.* 14:2795-2805 (1995). See also Kunkle, *Proc. Nat. Acad. Sci. USA* 82:488-492 (1985). Specifically, by utilizing oligonucleotide-directed mutagenesis, oligonucleotides were designed to "loop-out" a single Ig-like domain from the flt-1/IgG construct while also creating unique restriction sites at the boundaries of each of the seven Ig-like domains to be used for inserting other Ig-like domains obtained from other VEGF receptor extracellular ligand-binding regions for the purpose of creating other chimeric VEGF receptor molecules (see below). FIG. 2 presents the oligonucleotides used in generating Ig-like domain deletions from the flt-1/IgG construct and the restriction sites created as such. These experiments resulted in obtaining seven additional flt-1/IgG constructs, each having one of the seven different Ig-like domains deleted out.

To create the flt-1 Ig-like domain 1 deletion, the oligonucleotide 5'-AAATTAAAAGATCC<u>AGATCT</u>GACTATC-TATATATTTATTAGTGAT<u>ACCGGT</u>AGACCTTTT-3' (SEQ ID NO:39) was used to "loop-out" amino acids 36-123 and to introduce a Bgl II site and an Age 1 site at the 5'- and 3'-ends of the domain 1 deletion, respectively (see FIG. 2). Creation of the Bgl II site changed amino acid E33 to D.

The oligonucleotide used to create the flt-1Ig-like domain 2 deletion was 5'-GAAGGAAACAGAAG<u>GCGCC</u>ATC-TATATATTTATTCGA<u>GGTACC</u>AATACAATCATAG-3' (SEQ ID NO:40), effectively removing amino acids S129 through H223. The creation of Kas I and Kpn I restriction sites caused amino acid changes S122 to G and Q22S to occur, respectively.

Deletion of the third Ig-like domain removed amino acids N227 through S325 using the oligonucleotide 5'-CAAAC-TATCTCACACAT<u>AGATCT</u>ACCGTGCATATATATGAT-<u>ACCGGT</u>TTCATCACTGTGAAAC-3' (SEQ ID NO:41). Amino acids Q225, K331 and A332 were changed to S, T and G, respectively to accommodate for the insertion of Bgl II and Age I restriction sites.

The oligonucleotide 5'-GTTAACACCTCAGTGCACGT-GTATGATGTCAATGTGAAACCCCAGATCTACGAAA-AGGCCGTGTC-3' (SEQ ID NO:42) was used to loop-out amino acids K331 through I423 (flt-1 Ig-like domain 4 deletion). The amino acid change resulting from the generation of Bbr PI restriction site was I328 to V. Constituting a Bgl II restriction site at the 3' end of Ig-like domain 4 did not alter any amino acids.

Deleting Ig-like domain 5 amino acids K427 through S549 was achieved utilizing the oligonucleotide 5'-AAACCT-CACTGCCAC<u>GCTAGC</u>TGTCAATGTGTTTTATATCAC-<u>AGATCT</u>GCCAAATGGGTTTCAT-3' (SEQ ID NO:43).

Devising an Nhe 1 restriction site at the 5' end mutated I423 to A; amino acid V555 was substituted by L during the insertion of the Bgl II site in the 3' end.

To generate the Ig-like domain 6 deletion mutant, the oligonucleotide 5'-CCAGAAGAAAGAAATTAC<u>GTACG</u>AG-ATCTCACTGTTCAA<u>GGTACC</u>TCGGACAAGTCTAAT-3' (SEQ ID NO:45), did cause an amino acid substitution at I655 into V.

The last flt-1 Ig-like domain to be deleted, domain 7, removed amino acids Q658 through Y745 while adding restriction site Bsi WI and Kpn I 5' and 3', respectively. The oligonucleotide, 5'-CCAGAAGAAAGAAATTAC-<u>CGTACG</u>AGATCTCACTGTTCAA<u>GGTACC</u>TCGGA-CAAGTCTAAT-3', did cause an amino acid substitution at I655 into V.

Following construction of the flt-1/IgG construct and the Ig-like domain deletion constructs based on flt-1/IgG, the constructs were independently transformed into E. coli strain XL-1 Blue using techniques well known in the art. Following transformation of the constructs into E. coli strain XL-1 Blue, colonies were tested via restriction digestion for the presence of the newly created restriction sites shown in FIG. 2 and subsequently the entire coding region of each construct was sequenced using the Sequenase version 2.0 kit (US Biochemical Corp.). Double-stranded DNA for each selected clone was prepared using the QIAGEN DNA purification kit (Qiagen Inc.) and was used for transfection into CEN4 cells.

Plasmid DNA coding for the native flt-1/IgG protein or the flt-1 IgG domain deletions was introduced into CEN4 cells by calcium phosphate precipitation (Current protocols in Molecular Biology). CEN4 cells are a derivative of the human embryonic kidney 293 cell line that expresses the Epstein-Barr virus nuclear antigen-1, required for episomal replication of the pHEBO23 vector upon which the flt-1/IgG construct is based. Su et al., *Proc. Natl. Acad. Sci. USA* 88:10870-10874 (1991). Ten μg of plasmid DNA was used for transfection of a single 80% confluent 10 mm cell culture dish. Forty-eight hours post-transfection, the media containing the soluble chimeric VEGF receptors was collected and the concentration of protein produced was determined by ELISA assays designed to detect the $F_c$ portion of the chimeric protein.

EXAMPLE 2

Binding Assays for Detecting Binding to the VEGF Ligand

Binding assays with the soluble chimeric VEGF receptors generated in Example 1 above were performed essentially as described by Park et al., *J. Biol. Chem.* 269:25646-25654 (1994). Specifically, binding assays were performed in ninety-six-well breakaway immunoabsorbent assay plates (Nunc) coated overnight at 4° C. with 2 μg/ml affinity-purified goat anti-human $F_c$ IgG (Organon-Teknika) in 50 mM $Na_2CO_3$, pH 9.6. Plates were blocked for 1 hr with 10% fetal bovine serum in PBS (buffer B). After removal of the blocking buffer, 100 μl of a binding cocktail was added to each well. Binding cocktails consisted of a given amount of an flt-1/IgG chimeric protein, $^{125}I$-$VEGF_{165}$ (<9000 cpm/well), plus or minus 50 ng of unlabeled VEGF competitor where indicated, all within buffer B for a final volume of 100 μl; the cocktails were assembled and allowed to equilibrate overnight at 4° C. $VEGF_{165}$ was iodinated by the chloramine T method as previously described by Keyt et al., *J. Biol. Chem.* 271:5838-5646 (1998). The specific activity of the iodinated VEGF was $5.69 \times 10^7$ cpm/microgram. Incubation in the coated wells proceeded for 4 hrs at room temperature, followed by 4 washes with buffer B. Binding was determined by counting individual wells in a gamma counter. Data was analyzed using a 4-parameter non-linear curve fitting program (Kalidagraph, Abelbeck Software).

The results of the binding assays employing the intact flt-1/IgG chimeric protein and the seven flt-1/IgG Ig-like deletion chimeric proteins are presented in FIG. 3. As shown in FIG. 3, of all of the chimeric proteins tested, only the chimeric protein lacking the Ig-like domain 2 was unable to bind the VEGF ligand specifically. All of the other six flt-1/IgG deletion chimeras tested, as well as the intact flt-1/IgG chimera, retained the ability to bind the VEGF ligand specifically. These results demonstrate that the Ig-like domain 2 of the flt-1 extracellular ligand-binding region is required for specific binding to the VEGF ligand.

These results lead to the cloning, expression and testing of various other flt-1/IgG deletion chimeric constructs. Specific Ig-like domain/IgG constructs were created by amplifying the specific Ig-like domains desired, using PCR primers containing restrictions sites (Cla I and Bst BI, 5' and 3', respectively) which provided the in-frame sites to clone into the 5' end of the IgGl heavy chain cDNA plasmid (see Capon et al., *Nature* 337:525-531 (1989)). This resulted in the construction of an flt-1/IgG deletion construct having only Ig-like domains 1 and 2 of the flt-1 extracellular ligand-binding region fused to the Fc of IgG [flt(1,2)]. For the construction of flt(1,2), amino acids M1 through Q224 were amplified using oligonucleotides 5'-CAGGTCAATC<u>ATCGAT</u>GGT-CAGCTACTGGGACACC-3' (SEQ ID NO:46) (Flt. Cla I) and 5'-GGTCAACTAT<u>TTCGAA</u>TTGTCGATGTGTG-AGATAG-3' (SEQ ID NO:47) (Flt.2C.Bst BI).

Other flt-1/IgG deletion chimeras were also similarly prepared and contained the combination of Ig-like domain 2 only [flt(2)], Ig-like domains 2 and 3 only [flt(2,3)] and Ig-like domains 1, 2 and 3 only [flt(1,2,3)]. The same two oligonucleotides used to crease flt(1,2) were also used to create flt(2) from a construct lacking Ig-like domain 1. Flt(2,3) was generated by amplifying a construct lacking Ig-like domain 1 with the Flt.sp.Cla I oligonucleotide and another oligonucleotide 5'-GGTCAACTATTTCGAATATATG-CACTGAGGTGTTAAC-3' (SEQ ID NO:48) (Flt.3C.Bst BI) which includes the coding sequence through I328. Amplifying flt-1 Ig-like domains 1 through 3 was accomplished using primers Flt.sp.Cla I and Flt.3C.Bst BI on a construct having all three Ig-like domains. The entire domain-IgG coding sequence was then subcloned into pHEBO23 at the Cla I and Not I sites.

All of these flt-1/IgG chimera constructs were cloned, expressed and tested for their ability to specifically bind to VEGF as described above in Examples 1 and 2. As with the other flt-1/IgG constructs, all of these flt-1 IgG deletion constructs were sequenced, transfected into CEN4 cells and the expressed protein quantitated by $F_c$ ELISA. The results of the VEGF binding assays with the flt-1/IgG domain deletion chimeras is presented in FIG. 4.

The results presented in FIG. 4 demonstrate that flt-1 Ig-like domain 2 by itself is insufficient to allow binding of the VEGF ligand. Ig-like domain 1 in combination with domain 2 was also not sufficient to allow binding of the VEGF ligand. A small amount of VEGF-binding could be detected when Ig-like domains 2 and 3 were present in combination, but the extent and affinity of this binding needs to be further analyzed. In contrast, however, the ability to bind the VEGF ligand was completely restored when Ig-like domains 1, 2 and 3 were all three present in combination. These results, therefore, demonstrate that the combination of flt-1 Ig-like domains 1, 2 and 3 is sufficient for VEGF binding.

Next, increasing amounts of unlabeled VEGF ligand was used to titrate $^{125}$I-VEGF$_{165}$ binding to 1 ng of immunoreactive flt-1/IgG or flt(1,2,3). Binding assays were performed essentially as described above. The results from these experiments are presented in FIG. 5. Using the 4 P logistic curve fit: [(m1−m4)/(1+(m0/m3)^m2)]+m4, the value of m3 equals the concentration resulting in 50% inhibition (IC$_{50}$). This occurs at the point of inflection of the curve. As is shown in FIG. 5, the IC$_{50}$ for the intact flt-1/IgG chimeric protein and flt(1,2,3) deletion chimera is similar at 1.89 ng/ml and 1.34 ng/ml, respectively. Thus, the flt(1,2,3) deletion chimera behaves in a similar fashion to the intact flt-1/IgG chimeric protein with respect to binding to the VEGF ligand.

EXAMPLE 3

Binding Assays for Detecting Binding by "Swap" Chimeras to the VEGF Ligand

As shown in FIGS. 1A and 1B, the boundaries for each of the seven Ig-like domains present within the extracellular ligand-binding regions of the flt-1, KDR and FLT4 receptors were determined. Based on this information, various "swap" chimeras were prepared where one or more of the Ig-like domains from the flt-1/IgG construct were replaced with the same Ig-like domains from either the KDR or FLT4 receptor. In order to construct these "swap" chimeras, the desired domain fragment from either the KDR or FLT4 receptor was amplified using PCR primers which contained the same flanking restriction sites in frame as were created during the construction of the intact flt-1 IgG construct described above. Cleaving both the intact flt-1/IgG construct and the PCR fragment obtained from the amplification of the KDR or FLT4 receptor DNA with the restriction enzymes and subsequent ligation of the resulting fragments yielded constructs coding for the desired "swap" chimeras. All chimeric constructs produced were sequenced to confirm their authenticity.

In one experiment, the Ig-like domain 2 of either the KDR or FLT4 receptor was "swapped" for the Ig-like domain 2 of the flt-1/IgG construct to produce "swap" chimeras having flt-1 Ig-like domains 1 and 3-7 in combination with Ig-like domain 2 from either KDR (flt.K2) or FLT4 (fltF4.2). As before, both "swap" constructs were sequenced prior to transfection into and expression in CEN4 cells and the "swap" chimeras produced by the CEN4 cells were subjected to F$_c$ ELISA. The chimeric proteins were then tested as described above for their ability to specifically bind to $^{125}$I-VEGF$_{165}$. The results are presented in FIG. 6.

The results presented in FIG. 6 demonstrate that replacing the flt-1 Ig-like domain 2 with the Ig-like domain 2 of the KDR receptor functions to re-establish the ability to specifically bind to the VEGF ligand whereas the presence of FLT4 Ig-like domain 2 did not re-establish the ability to specifically bind to the VEGF ligand. Since it is known that native FLT4 receptor does not bind to the VEGF ligand and since the KDR receptor does interact with this ligand, these results demonstrate that Ig-like domain 2 is the primary domain responsible for VEGF binding. Expectedly, the native flt-1/IgG chimera specifically bound to the VEGF ligand whereas the flt-1/IgG chimera lacking an Ig-like domain 2 did not specifically bind to the VEGF ligand.

Next, experiments were performed to determine if the specificity for binding to the VEGF ligand resides in the Ig-like domain 2 of the flt-1 and KDR receptors. Specifically, it is well known that placenta growth factor (PLGF) is capable of binding to the extracellular ligand-binding region of the flt-1 receptor but does not bind to the extracellular ligand-binding regions of either the KDR or FLT4 receptors. Thus, binding of PLGF can compete with binding of the VEGF ligand to the flt-1 receptor.

Based on this information, a competition against VEGF binding was performed using a series of "swap" mutants that consisted of the flt-1/IgG chimeric protein wherein various Ig-like domains thereof were replaced with the same Ig-like domains from the KDR receptor. Specifically, "swap" chimeras were constructed as described above wherein either Ig-like domain 1, 2, 3, 5 or 7 of the flt-1/IgG chimera was replaced by the corresponding Ig-like domain from the KDR receptor. Competition binding assays were performed as described above wherein competitors consisted of 50 ng of unlabeled VEGF or 50 ng of unlabeled PLGF. The results of these competition binding assays are presented in FIG. 7.

The results presented in FIG. 7 demonstrate that only when the Ig-like domain 2 of the flt-1 receptor is replaced with the Ig-like domain 2 of the KDR receptor is the VEGF interaction more like wild type KDR than wild type flt-1. Each of the other "swap" chimeras constructed behaved similar to the wild type flt-1 receptor. Moreover, when the Ig-like domain 2 of the flt-1/IgG chimeric protein was replaced by the Ig-like domain 2 of the FLT4 receptor, the resulting chimeric protein exhibited the binding specificity of the intact FLT4 receptor (data not shown). These results demonstrate, therefore, that the Ig-like domain 2 of the flt-1 and KDR receptors is the major determinant of ligand specificity.

Next, an expression construct encoding the entire human FLT4 receptor, including the extracellular domain, transmembrane region and intracellular tyrosine kinase domain (Lee et al., *Proc. Natl. Acad. Sci. USA* 93:1988-1992 (1996)) was used to create various other chimeric receptors. The construct encoding the entire FLT4 receptor was then subjected to oligo-directed mutagenesis as described above to create in-frame restriction sites located at the beginning of the Ig-like domain 1 of the FLT4 extracellular ligand-binding region (Afl II), the end of domain 1/beginning of domain 2 (Nhe I), the end of domain 2/beginning of domain 3 (Bsi WI), and the end of domain 3 (Mlu I). The following flt-1 Ig-like domain combinations were then amplified essentially as described above using PCR primers that possessed the same in-frame restriction sites: domain 2 alone and domains 1-3 alone. Cloning the flt-1 PCR products into the mutagenized FLT4 encoding construct resulted in flt-1/FLT4 chimeric receptor constructs.

Specifically, constructs were prepared which possessed the entire FLT4 receptor sequences except that the FLT4 Ig-like domains 1-3 were replaced with the Ig-like domains 1-3 of the flt-1 receptor (construct flt-1(1,2,3)/FLT4) or that the FLT4 Ig-like domain 2 was replaced with the Ig-like domain 2 of the flt-1 receptor (construct flt-1(2)/FLT4). For flt-1(1,2,3)/FLT4, FLT4 sequence encoding amino acids N33 through E324 was replaced by flt-1 sequences encoding S35 through S325. Creation of the cloning sites resulted in a change of I325 of FLT4 to R. For flt-1 (2)/FLT4, FLT4 sequence encoding S128 through 1224 was replaced by flt-1 sequence encoding 1124 through R224. This also changes FLT4 amino acids N33 and I326 to S and R, respectively and added T36. Sequencing confirmed the authenticity of these chimeras. FIGS. 8, 9 and 10 (SEQ ID NOS:32-34) show the entire amino acid sequences of the intact FLT4 receptor, the entire amino acid sequence of the chimeric receptor encoded by the flt-1(1,2,3)/FLT4 construct and the entire amino acid sequence of the chimeric receptor encoded by the flt-1(2)/FLT4 construct, respectively.

After preparation of these expression constructs, 293 cells were transfected with the constructs via DEAE-Dextran and transiently-expressing cells were analyzed for the ability to bind to the VEGF ligand. To detect binding of the VEGF ligand, a saturation binding assay was performed on transiently-expressing 293 cells expressing the intact FLT4 receptor, the flt-1 domain 2/FLT4 chimeric receptor, the flt-1 domains 1-3/FLT4 chimeric receptor, or the intact flt-1 receptor. Specifically, $2.5 \times 10^5$ cells were incubated with increasing amounts of $^{125}$I-VEGF (specific activity of $56.9 \times 10^6$ cpm/μg) in a final volume of 0.2 mls of buffer C (50/50 media with 0.1% BSA and 25 mM HEPES pH 7.3) for 4 hrs at 4° C. with slight agitation. The cell mixture was then layered over a 0.75 ml cushion of 30% sucrose, centrifuged for 10 minutes at maximum speed, and the pellet was recovered and counted in a gamma counter. Because 293 cells possess some flt-1-like VEGF binding, non-transfected cells were also used and the background counts were subtracted out from the counts recovered for the transfected cells. The amount of counts added and the recovered counts bound were then subjected to scatchard analysis.

The results of these experiments demonstrated that, as expected, the cells expressing the intact FLT4 receptor did not specifically bind the VEGF ligand. However, cells expressing the flt-1 domain 2/FLT4 chimeric receptor or the flt-1 domains 1-3/FLT4 chimeric receptor did specifically bind the VEGF ligand specifically and tightly. The Kds are approximately 10.2 pM+/−1.1 pM and 10.4 pM+/−3.4 pM, respectively, for the flt-1 domain 2/FLT4 chimeric receptor and the flt-1 domains 1-3/FLT4 chimeric receptor. These values are near the range reported for the intact full-length flt-1 receptor.

Experiments were also performed to measure the amount of tyrosine phosphorylation in 293 cells transiently expressing these chimeric receptors 60-72 hours post-transfection. Tyrosine phosphorylation assays were performed essentially as described in Park et al., *J. Biol. Chem.* 269:25646-25654 (1994). The transiently expressing 293 cells were deprived of serum 16-18 hrs prior to stimulation by a given factor. Cells were stimulated with FLT4 ligand (VH1.4.5; VEGF-C/VRP) at a concentration of 400 ng/ml, 50 ng/ml VEGF, or 0.5 nM PLGF for 15 minutes at 37° C. Following removal of the stimulation media, the cells were twice washed with ice-cold PBS and then lysed in 1 ml lysis buffer. The lysate was cleared of cellular debris and the receptors were immunoprecipitated using JTL.1, a polyclonal antibody directed against the extracellular domain of the FLT4 receptor (see Lee et. al., *Proc. Natl. Acad. Sci USA*, 93:1988-1992 (1996)). The immunoprecipitates were then subjected to western gel/blot analysis using the 4G10 anti-phosphotyrosine monoclonal antibody (UBI, Lake Placid, N.Y.). Immunoreactive bands were visualized with an ABC kit according to manufacturers directions (Vector Laboratories).

To establish stable cell lines, each of the chimeric constructs was co-transfected with a plasmid containing the neomycin resistance gene via calcium phosphate precipitation into NIH 3T3 cells. Clones proliferating in the presence of G418 were screened for their ability to bind to VEGF. Clones expressing either the flt-1 (1,2,3)/FLT4 or flt-1 (2)/FLT4 chimera were analyzed in a cell binding assay to determine the Kd for VEGF by titrating a trace amount of $^{125}$I-VEGF$_{165}$ (approx. 5000 cpm/ml final) with increasing amounts of cold VEGF$_{165}$. First the adherent cells were washed with cold binding buffer C (DMEM/F12 media with 0.2% BSA and 25 mM HEPES, pH 7.4), then $^{125}$I-VEGF$_{165}$ and the cold competitor, each in 0.5 mls buffer C, were added simultaneously. The cells were then placed at 4° C. for 4 hours. After aspirating off the binding buffer, the cells were washed with cold PBS and then twice with cold PBS containing 2M NaCl. Finally, the cells were lysed with 0.25M NaOH and the entire lysate was counted in a gamma counter. Results were analyzed and the Kds calculated using the Scatchard analysis program New Ligand (Genentech, Inc.).

NIH 3T3 cells stably expressing either the flt-1 (1,2,3)/FLT4 or the flt-1 (2)FLT4 chimeric receptors were plated in 12-well format at 50,000 cells/well in low glucose DMEM media containing 10% FBS, 100 units/ml Penicillin-Streptomycin (Gibco BRL), 2 mM Glutamine, 2.5 microgram/ml Fungizone (Gibco BRL), and 200 micrograms/ml G418 (Gibco BRL). Following 18-24 hours of serum starvation in media containing 0.5% FBS, growth factors or 10% FBS were added. The concentration of VEGF$_{165}$ added ranged from 5 pg/ml to 300 ng/ml; PlGF$_{152}$ concentrations were between 5.12 ng/ml and 3.2 micrograms/ml; the concentration of VEGF-C was 40 ng/ml and 4 micrograms/ml. Following stimulation for 12-16 hours at 37° C., [$^3$H]thymidine (1 mCi/ml; 5 Ci/mmol) was added for a final concentration of 1 microcurie/ml and incubation proceeded at 37° C. for 4 hours. Removal of the media and several PBS washes was succeeded by TCA precipitation. Following the removal of TCA, cells were then lysed with 0.2N NaOH, 1% SDS, transferred to scintillation vials and neutralized with 2M Na$_2$OAc, pH 4.0. The samples were counted using the tritium channel.

The results of these experiments demonstrated that while VEGF did not stimulate tyrosine phosphorylation in cells transiently expressing the intact FLT4 receptor, significant tyrosine phosphorylation was observed in cells transiently expressing the flt-1 (2)/FLT4 chimeric receptor or the flt-1 (1,2,3)/FLT4 chimeric receptor. Thus, these experiments demonstrate that the flt-1 (2)/FLT4 chimeric receptor and the flt-1 (1,2,3)/FLT4 chimeric receptor are able to bind and specifically respond to VEGF. Moreover, these clones showed a significant response to VEGF in the thymidine incorporation assay.

CONCLUDING REMARKS

The foregoing description details specific methods which can be employed to practice the present invention. Having detailed such specific methods, those skilled in the art will well enough known how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed is:

1. A method of inhibiting vascularization or angiogenesis comprising administering a chimeric VEGF receptor protein comprising immunoglobulin (Ig)-like domains from two or more different VEGF receptor molecules, wherein said chimeric VEGF receptor protein comprises Ig-like domain 2 of flt-1 receptor or KDR receptor.

2. The method of claim 1, wherein the Ig-like domain 2 comprises the amino acid sequence of SEQ ID NO:49.

3. The method of claim 1, wherein the Ig-like domain 2 comprises the amino acid sequence of SEQ ID NO:50.

4. The method of claim 1, wherein the chimeric VEGF receptor protein further comprises Ig-like domain 3 of a flt-1 receptor or a KDR receptor.

5. The method of claim 4, wherein the Ig-like domain 3 comprises the amino acid sequence of SEQ ID NO:51.

6. The method of claim 4, wherein the Ig-like domain 3 comprises the amino acid sequence of SEQ ID NO:52.

7. The method of claim 4, wherein the Ig-like domain 2 comprises the amino acid sequence of SEQ ID NO:49 and the Ig-like domain 3 comprises the amino acid sequence of SEQ ID NO:52.

8. The method of claim 4, wherein the Ig-like domain 2 comprises the amino acid sequence of SEQ ID NO:50 and the Ig-like domain 3 comprises the amino acid sequence of SEQ ID NO:52.

9. The method of claim 4, wherein the Ig-like domain 2 comprises the amino acid sequence of SEQ ID NO:50 and the Ig-like domain 3 comprises the amino acid sequence of SEQ ID NO:51.

10. The method of claim 4, wherein the Ig-like domain 2 comprises the amino acid sequence of SEQ ID NO:49 and the Ig-like domain 3 comprises the amino acid sequence of SEQ ID NO:51.

11. The method of claim 1, wherein the chimeric VEGF receptor protein inhibits VEGF mitogenic activity.

12. The method of claim 1, wherein the chimeric VEGF receptor protein comprises the amino acid sequence of Flt-1 and/or KDR linked to an immunoglobulin sequence.

13. The method of claim 12, wherein the immunoglobulin sequence comprises the IgG heavy chain sequence.

14. A method of inhibiting proliferation of an endothelial cell, comprising administering a chimeric VEGF receptor protein comprising immunoglobulin (Ig)-like domains from two or more different VEGF receptor molecules, wherein said chimeric VEGF receptor protein comprises Ig-like domain 2 of flt-1 receptor or KDR receptor.

15. The method of claim 14, wherein the Ig-like domain 2 comprises the amino acid sequence of SEQ ID NO:49.

16. The method of claim 14, wherein the Ig-like domain 2 comprises the amino acid sequence of SEQ ID NO:50.

17. The method of claim 14, wherein the chimeric VEGF receptor protein further comprises Ig-like domain 3 of a flt-1 receptor or a KDR receptor.

18. The method of claim 17, wherein the Ig-like domain 3 comprises the amino acid sequence of SEQ ID NO:51.

19. The method of claim 17, wherein the Ig-like domain 3 comprises the amino acid sequence of SEQ ID NO:52.

20. The method of claim 17, wherein the Ig-like domain 2 comprises the amino acid sequence of SEQ ID NO:49 and the Ig-like domain 3 comprises the amino acid sequence of SEQ ID NO:52.

21. The method of claim 17, wherein the Ig-like domain 2 comprises the amino acid sequence of SEQ ID NO:50 and the Ig-like domain 3 comprises the amino acid sequence of SEQ ID NO:52.

22. The method of claim 17, wherein the Ig-like domain 2 comprises the amino acid sequence of SEQ ID NO:50 and the Ig-like domain 3 comprises the amino acid sequence of SEQ ID NO:51.

23. The method of claim 17, wherein the Ig-like domain 2 comprises the amino acid sequence of SEQ ID NO:49 and the Ig-like domain 3 comprises the amino acid sequence of SEQ ID NO:51.

24. The method of claim 14, wherein the chimeric VEGF receptor protein inhibits VEGF mitogenic activity.

25. The method of claim 14, wherein the chimeric VEGF receptor protein comprises the amino acid sequence of Flt-1 and/or KDR linked to an immunoglobulin sequence.

26. The method of claim 25, wherein the immunoglobulin sequence comprises the IgG heavy chain sequence.

27. A method of treating a condition or disorder characterized by undesired vascularization, comprising administering a chimeric VEGF receptor protein comprising immunoglobulin (Ig)-like domains from two or more different VEGF receptor molecules, wherein said chimeric VEGF receptor protein comprises Ig-like domain 2 of flt-1 receptor or KDR receptor.

28. The method of claim 27, wherein the condition or disorder comprises a neoplastic condition or disorder.

29. The method of claim 28, wherein the neoplastic condition or disorder comprises breast, lung, esophagus, gastric, colon, rectum, liver, ovary, cervix, prostate, pancreas, renal, or endometrium carcinoma.

30. The method of claim 28, wherein the neoplastic condition or disorder comprises thecoma, arrhenoblastoma, endometrial hyperplasia, endometriosis, fibrosarcoma, choriocarcinoma, head cancer, neck cancer, nasopharyngeal carcinoma, laryngeal carcinoma, hepatoblastoma, Karposi's sarcoma, melanoma, skin carcinoma, hemangioma, hemangioblastoma, retinoblastoma, astrocystoma, glioblastoma, Schwannoma, oligodendroglioma, medulloblastoma, neuroblastoma, rhabdomyosarcoma, osteogenic sarcoma, leiomyosarcomas, urinary tract carcinoma, thyroid carcinoma, Wilm's tumor, abnormal vascular proliferation associated with phakomatoses, and Meigs' syndrome.

31. The method of claim 27, wherein the condition or disorder comprises a non-neoplastic condition or disorder.

32. The method of claim 31, wherein the non-neoplastic condition or disorder comprises rheumatoid arthritis, psoriasis, atherosclerosis, diabetic retinopathy, retrolentral fibroplasia, neovascular glaucoma, age-related macular degeneration, thyroid hyperplasia, corneal transplantation, chronic inflammation, lung inflammation, nephrotic syndrome, preclampsia, ascites, pericardial effusion, or pleural effusion.

33. The method of claim 27, wherein the Ig-like domain 2 comprises the amino acid sequence of SEQ ID NO:49.

34. The method of claim 27, wherein the Ig-like domain 2 comprises the amino acid sequence of SEQ ID NO:50.

35. The method of claim 27, wherein the chimeric VEGF receptor protein further comprises Ig-like domain 3 of a flt-1 receptor or a KDR receptor.

36. The method of claim 35, wherein the Ig-like domain 3 comprises the amino acid sequence of SEQ ID NO:51.

37. The method of claim 35, wherein the Ig-like domain 3 comprises the amino acid sequence of SEQ ID NO:52.

38. The method of claim 35, wherein the Ig-like domain 2 comprises the amino acid sequence of SEQ ID NO:49 and the Ig-like domain 3 comprises the amino acid sequence of SEQ ID NO:52.

39. The method of claim 35, wherein the Ig-like domain 2 comprises the amino acid sequence of SEQ ID NO:50 and the Ig-like domain 3 comprises the amino acid sequence of SEQ ID NO:52.

40. The method of claim 35, wherein the Ig-like domain 2 comprises the amino acid sequence of SEQ ID NO:50 and the Ig-like domain 3 comprises the amino acid sequence of SEQ ID NO:51.

41. The method of claim 35, wherein the Ig-like domain 2 comprises the amino acid sequence of SEQ ID NO:49 and the Ig-like domain 3 comprises the amino acid sequence of SEQ ID NO:51.

42. The method of claim 27, wherein the chimeric VEGF receptor protein inhibits VEGF mitogenic activity.

43. The method of claim 27, wherein the chimeric VEGF receptor comprises the amino acid sequence of Flt-1 and/or KDR linked to an immunoglobulin sequence.

44. The method of claim 43, wherein the immunoglobulin sequence comprises the IgG heavy chain sequence.

* * * * *

UNITED STATES PATENT AND TRADEMARK OFFICE
CERTIFICATE OF CORRECTION

| | |
|---|---|
| PATENT NO. | : 7,771,721 B2 |
| APPLICATION NO. | : 12/104825 |
| DATED | : August 10, 2010 |
| INVENTOR(S) | : Terri Lynn Davis-Smyth et al. |

It is certified that error appears in the above-identified patent and that said Letters Patent is hereby corrected as shown below:

On the title page, in the Related U.S. Application Data, Item (60) cancel the text "application No. 11/537,623, filed on Sep. 30, 2006, which is a continuation of".

In the Abstract, Item (57), line 7, replace "anglogenic" with -- angiogenic --.

In the References Cited, Item (56), replace "Quinn et al., 1993, *Proc. Natl. Acad. Set USA*" with -- Quinn et al., 1993, *Proc. Natl. Acad. Sci. USA* --.

In the References Cited, Item (56), replace "DeVries et al., 1992, *Science*, 225:989-991" with -- DeVries et al., 1992, *Science*, 255:989-991 --.

Col. 1, lines 8-9, cancel the text "application Ser. No. 11/537,623 filed Sep. 30, 2006, which is a continuation of".

Col. 2, line 38, replace "DeVries, et al., *Science*, 226:989-991 (1992)" with -- DeVries, et al., *Science*, 255:989-991 (1992) --.

Col. 5, lines 2-4, replace ""●" designates binding by the flt(1,2,3) deletion chimera. "♦" designates binding by the intact flt-1/IgG chimeric protein" with -- "●" designates binding by the intact flt-1/IgG chimeric protein. "♦" designates binding by the flt(1,2,3) deletion chimera --.

Col. 7, line 18, replace "al. *J. Mol. Biol.* 53, 164 (1970)" with -- al. *J. Mol. Biol.* 53, 159 (1970) --.

Col. 7, line 27, replace "Hsiao, C. L., et al. *Proc. Ned. Acad. Sci.*" with -- Hsiao, C. L., et al. *Proc. Natl. Acad. Sci.*--.

Col. 9, line 3, replace "*Nucleic Acids Res.* 9, 6103-8114 (1981)" with -- *Nucleic Acids Res.* 9, 6103-6114(1981) --.

Signed and Sealed this
Eleventh Day of October, 2011

David J. Kappos
*Director of the United States Patent and Trademark Office*

CERTIFICATE OF CORRECTION (continued)

U.S. Pat. No. 7,771,721 B2

TABLE 1, at col. 12, line 53, replace "The (T)" with -- Thr (T) --.

Col. 13, lines 7-8, replace "(a) a residue having an electronegative" with -- (e) a residue having an electronegative --.

Col. 16, line 30, replace "Chasin, *Proc. Natl. Aced. Sci. (USA)*" with -- Chasin, *Proc. Natl. Acad. Sci. (USA)* --.

Col. 17, line 16, replace "*Aced. Sci. USA* 77:2197 (1980)" with -- *Acad. Sci. USA* 77:2197 (1980) --.

Col. 17, line 19, replace "*Natl. Aced. Sci. USA* 81:6851 (1984)" with -- *Natl. Acad. Sci. USA* 81:6851 (1984) --.

Col. 17, line 27, replace "Gascoigne et al., *Proc. Natl. Aced. Sci. USA*" with -- Gascoigne et al., *Proc. Natl. Acad. Sci. USA* --.

Col. 20, line 54, replace "Karposi's" with -- Kaposi's --.

Col. 20, line 60, replace "Wilm's" with -- Wilms' --.

Col. 21, line 1, replace "grave's" with -- Graves' --.

Col. 21, line 3, replace "preclampasia" with -- preeclampsia --.

Col. 22, lines 34-37, replace "To create the flt-1 Ig-like domain 1 deletion, the oligonucleotide 5'-AAATTAAAAGATCCAGATCTGACTATCTATATATTTATTAGTGATACCGGTAGACCTTTT-3' (SEQ ID NO:39) was used to "loop-out" amino acids 36-123" with -- To create the flt-1 Ig-like domain 1 deletion, the oligonucleotide 5'-AAAATTAAAAGATCCAGATCTGACTATCTATATATTTATTAGTGAT ACCGGTAGACCTTTT-3' (SEQ ID NO:39) was used to "loop-out" amino acids 36-123 --.

Col. 22, lines 45-46, replace "The creation of Kas I and Kpn I restriction sites caused amino acid changes S122 to G and Q22S to" with -- The creation of Kas I and Kpn I restriction sites caused amino acid changes S122 to G and Q225 to G to --.

Col. 22, lines 55-60, replace "The oligonucleotide 5'-GTTAACACCTCAGTGCA CGTGTATGATGTCAATGTGAAACCCCAGATCTACGAAAAGGCCGTGTC-3' (SEQ ID NO:42) was used to loop-out amino acids K331 through I423 (flt-1 Ig-like domain 4 deletion). The amino acid change resulting from the generation of Bbr PI restriction site was 1328 to V" with -- The oligonucleotide 5'-GTTAACACCTCAGTGCACGTGTATGATGTCAATGTGAAACCCCAGATCT ACGAAAAGGCCGTGTC-3' (SEQ ID NO:42) was used to loop-out amino acids K331 through I423 (flt-1 Ig-like domain 4 deletion). The amino acid change resulting from the generation of Bbr PI restriction site was I328 to V --.

CERTIFICATE OF CORRECTION (continued)
U.S. Pat. No. 7,771,721 B2

Col. 23, lines 4-15, replace:

"To generate the Ig-like domain 6 deletion mutant, the oligonucleotide 5'-CCAGAAGAAAGAAATTA<u>CGTACG</u>AGATCTCACTGTTCAA<u>GGTACCT</u>CG GACAAGTCTAAT-3' (SEQ ID NO:45), did cause an amino acid substitution at I655 into V.

The last flt-1 Ig-like domain to be deleted, domain 7, removed amino acids Q658 through Y745 while adding restriction site Bsi WI and Kpn I 5' and 3', respectively. The oligonucleotide, 5'-CCAGAAGAAAGAAATTA<u>CGTACG</u>AGATCTCACTGTTCAA<u>GGTACC</u>TCGGACAAGTCTAAT-3', did cause an amino acid substitution at I655 into V"

with

--To generate the Ig-like domain 6 deletion mutant, the oligonucleotide 5'-GTGGGAAGAAACATAAGCTTT<u>GTATAC</u>ATTACAATC<u>AGATCT</u>CA GGAAGCACCATAC-3' (SEQ ID NO:44) excised the amino acids T553 through E652. Generating the Bst 1107I restriction site at the 5' end changed amino acids Y551 and I552 to V and Y, respectively; amino acid D657 was substituted by S during the formation of the Bgl II restriction site at the 3' end.

The last flt-1 Ig-like domain to be deleted, domain 7, removed amino acids Q658 through Y745 while adding restriction site Bsi WI and Kpn I 5' and 3', respectively. The oligonucleotide, 5'-CCAGAAGAAAGAAATTA<u>CGTACG</u>AGATCTCACTGTTCAA<u>GGTACC</u>TCGGACAAGTCTAAT-3' (SEQ ID NO:45), did cause an amino acid substitution at I655 into V --.

Col 23, lines 65-66, replace "Keyt et al., *J. Biol. Chem.* 271:5838-5646 (1998)" with -- Keyt et al., *J. Biol. Chem.* 271:5638-5646 (1996) --.

Col. 24, lines 24-25, replace "This resulted in the construction of an fit-l/IgG deletion construct" with -- This resulted in the construction of an flt-1/IgG deletion construct --.

Col. 24, line 32, replace "(SEQ ID NO:47) (Flt.2C.Bst BI)" with -- (SEQ ID NO:47) (Flt.2C.Bst BI) --.

Col. 24, lines 29-30, replace "using oligonucleotides 5'-CAGGTCAATCATCGATGGT-CAGCTACTGGGACACC-3' (SEQ ID NO:46) (Flt. Cla I)" with -- using oligonucleotides 5'-CAGGTCAATC<u>ATCGAT</u>GGTCAGCTACTGGGACACC-3' (SEQ ID NO:46) (Flt.sp.Cla I) --.

Col. 27, lines 1-6, replace "Creation of the cloning sites resulted in a change of I325 of FLT4 to R. For flt-1 (2)/FLT4, FLT4 sequence encoding S128 through I224 was replaced by flt-1 sequence encoding I124 through R224. This also changes FLT4 amino acids N33 and I326 to S and R, respectively and added T36" with -- Creation of the cloning sites resulted in a change of I325 of FLT4 to R. For flt-1 (2)/FLT4, FLT4 sequence encoding S128 through I224 was replaced by flt-1 sequence encoding I124 through R224. This also changes FLT4 amino acids N33 and I326 to S and R, respectively and added T36 --.

In claim 30, at col. 85, line 1, replace "Karposi's" with -- Kaposi's --.

In claim 30, at col. 85, line 7, replace "Winn's" with -- Wilms' --.

SEQUENCE LISTING (1) GENERAL INFORMATION:

(iii) NUMBER OF SEQUENCES: 52

(2) INFORMATION FOR SEQ ID NO: 1:

(i) SEQUENCE CHARACTERISTICS:
       (A) LENGTH: 758 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO: 1:

```
Met Val Ser Tyr Trp Asp Thr Gly Val Leu Leu Cys Ala Leu Leu Ser
1               5                   10                  15

Cys Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65              70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
            130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320
```

```
Ser Val Asn Thr Ser Val His Ile Tyr Asp Lys Ala Phe Ile Thr Val
            325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
            370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
            530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
            610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735
```

-continued

```
Lys Gly Ser Val Glu Ser Ser Ala Tyr Leu Thr Val Gln Gly Thr Ser
            740                 745                 750

Asp Lys Ser Asn Phe Glu
        755
```

(2) INFORMATION FOR SEQ ID NO: 2:

(i) SEQUENCE CHARACTERISTICS:
        (A) LENGTH: 767 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 2:

```
Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
            130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
            210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
            290                 295                 300

Tyr Thr Cys Ala Ala Ser Ser Gly Leu Met Thr Lys Lys Asn Ser Thr
305                 310                 315                 320
```

-continued

```
Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
```

-continued

```
                    740                 745                 750
Ile Ile Glu Gly Ala Gln Glu Lys Thr Asn Leu Asp Pro Phe Glu
            755                 760                 765
```

(2) INFORMATION FOR SEQ ID NO: 3:

(i) SEQUENCE CHARACTERISTICS:
        (A) LENGTH: 777 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 3:

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
```

-continued

```
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Glu Phe Gln Trp
            355                 360                 365
Tyr Lys Asp Gly Lys Ala Leu Ser Gly Arg His Ser Pro His Ala Leu
            370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
                420                 425                 430
Ser Ile Tyr Ser Arg His Ser Arg Gln Ala Leu Thr Cys Thr Ala Tyr
                435                 440                 445
Gly Val Pro Leu Pro Leu Ser Ile Gln Trp His Trp Arg Pro Trp Thr
            450                 455                 460
Pro Cys Lys Met Phe Ala Gln Arg Ser Leu Arg Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
                500                 505                 510
Gly Lys Asn Lys Thr Val Ser Lys Leu Val Ile Gln Asn Ala Asn Val
                515                 520                 525
Ser Ala Met Tyr Lys Cys Val Val Ser Asn Lys Val Gly Gln Asp Glu
            530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
            595                 600                 605
Asp Cys Lys Asn Val His Leu Phe Ala Thr Pro Leu Ala Ala Ser Leu
            610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
                660                 665                 670
Gln Ala Leu Glu Ala Pro Arg Leu Thr Gln Asn Leu Thr Asp Leu Leu
            675                 680                 685
Val Asn Val Ser Asp Ser Leu Glu Met Gln Cys Leu Val Ala Gly Ala
            690                 695                 700
His Ala Pro Ser Ile Val Trp Tyr Lys Asp Glu Arg Leu Leu Glu Glu
705                 710                 715                 720
Lys Ser Gly Val Asp Leu Ala Asp Ser Asn Gln Lys Leu Ser Ile Gln
                725                 730                 735
Arg Val Arg Glu Glu Asp Ala Gly Arg Tyr Leu Cys Ser Val Cys Asn
            740                 745                 750
```

```
Ala Lys Gly Cys Val Asn Ser Ser Ala Ser Val Ala Val Glu Gly Ser
        755                 760                 765

Glu Asp Lys Gly Ser Met Glu Val Thr
        770                 775

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 2..25

(xi) SEQUENCE DESCRIPTION: SEQ ID NO: 4:

A AAA TTA AAA GAT CCA GAT CTG AGT                                    25
  Lys Leu Lys Asp Pro Asp Leu Ser
   1               5

(2) INFORMATION FOR SEQ ID NO: 5:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 5:

Lys Leu Lys Asp Pro Asp Leu Ser
 1               5

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..36

(xi) SEQUENCE DESCRIPTION: SEQ ID NO: 6:

ATC TAT ATA TTT ATT AGT GAT ACC GGT AGA CCT TTT                      36
Ile Tyr Ile Phe Ile Ser Asp Thr Gly Arg Pro Phe
 1               5                  10

(2) INFORMATION FOR SEQ ID NO: 7:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 7:

Ile Tyr Ile Phe Ile Ser Asp Thr Gly Arg Pro Phe
 1               5                  10
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 2..34

(xi) SEQUENCE DESCRIPTION: SEQ ID NO: 8:

```
G AAG GAA ACA GAA GGC GCC ATC TAT ATA TTT ATT                        34
  Lys Glu Thr Glu Gly Ala Ile Tyr Ile Phe Ile
   1               5                  10
```

(2) INFORMATION FOR SEQ ID NO: 9:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 9:

```
Lys Glu Thr Glu Gly Ala Ile Tyr Ile Phe Ile
 1               5                  10
```

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..21

(xi) SEQUENCE DESCRIPTION: SEQ ID NO: 10:

```
CGA GGT ACC AAT ACA ATC ATA G                                        22
Arg Gly Thr Asn Thr Ile Ile
 1               5
```

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 11:

```
Arg Gly Thr Asn Thr Ile Ile
 1               5
```

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: unknown (D) TOPOLOGY: unknown (ii) MOLECULE TYPE: DNA (ix) FEATURE:
        (A) NAME/KEY: CDS
        (B) LOCATION: 3..26

(xi) SEQUENCE DESCRIPTION: SEQ ID NO: 12:

CA AAC TAT CTC ACA CAT AGA TCT ACC                                          26
   Asn Tyr Leu Thr His Arg Ser Thr
    1               5

(2) INFORMATION FOR SEQ ID NO: 13:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 13:

Asn Tyr Leu Thr His Arg Ser Thr
 1               5

(2) INFORMATION FOR SEQ ID NO: 14:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..36

(xi) SEQUENCE DESCRIPTION: SEQ ID NO: 14:

GTG CAT ATA TAT GAT ACC GGT TTC ATC ACT GTG AAA C                           37
Val His Ile Tyr Asp Thr Gly Phe Ile Thr Val Lys
 1               5                  10

(2) INFORMATION FOR SEQ ID NO: 15:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 15:

Val His Ile Tyr Asp Thr Gly Phe Ile Thr Val Lys
 1               5                  10

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..27

(xi) SEQUENCE DESCRIPTION: SEQ ID NO: 16:

GTT AAC ACC TCA GTG CAC GTG TAT GAT                                    27
Val Asn Thr Ser Val His Val Tyr Asp
  1               5

(2) INFORMATION FOR SEQ ID NO: 17:

(i) SEQUENCE CHARACTERISTICS:
           (A) LENGTH: 9 amino acids
           (B) TYPE: amino acid
           (D) TOPOLOGY: linear (ii) MOLECULE TYPE: protein (xi) SEQUENCE DESCRIPTION: SEQ ID NO: 17:

Val Asn Thr Ser Val His Val Tyr Asp
  1               5

(2) INFORMATION FOR SEQ ID NO: 18:

(i) SEQUENCE CHARACTERISTICS:
           (A) LENGTH: 38 base pairs
           (B) TYPE: nucleic acid
           (C) STRANDEDNESS: unknown
           (D) TOPOLOGY: unknown (ii) MOLECULE TYPE: DNA (ix) FEATURE:
           (A) NAME/KEY: CDS
           (B) LOCATION: 1..36

(xi) SEQUENCE DESCRIPTION: SEQ ID NO: 18:

GTC AAT GTG AAA CCC CAG ATC TAC GAA AAG GCC GTG TC                     38
Val Asn Val Lys Pro Gln Ile Tyr Glu Lys Ala Val
  1               5                  10

(2) INFORMATION FOR SEQ ID NO: 19:

(i) SEQUENCE CHARACTERISTICS:
           (A) LENGTH: 12 amino acids
           (B) TYPE: amino acid
           (D) TOPOLOGY: linear (ii) MOLECULE TYPE: protein (xi) SEQUENCE DESCRIPTION: SEQ ID NO: 19:

Val Asn Val Lys Pro Gln Ile Tyr Glu Lys Ala Val
  1               5                  10

(2) INFORMATION FOR SEQ ID NO: 20:

(i) SEQUENCE CHARACTERISTICS:
           (A) LENGTH: 31 base pairs
           (B) TYPE: nucleic acid
           (C) STRANDEDNESS: unknown
           (D) TOPOLOGY: unknown (ii) MOLECULE TYPE: DNA (ix) FEATURE:
           (A) NAME/KEY: CDS
           (B) LOCATION: 2..31

(xi) SEQUENCE DESCRIPTION: SEQ ID NO: 20:

A AAC CTC ACT GCC ACG CTA GCT GTC AAT GTG                              31
  Asn Leu Thr Ala Thr Leu Ala Val Asn Val
    1               5                  10

(2) INFORMATION FOR SEQ ID NO: 21:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 21:

```
Asn Leu Thr Ala Thr Leu Ala Val Asn Val
 1               5                  10
```

(2) INFORMATION FOR SEQ ID NO: 22:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..33

(xi) SEQUENCE DESCRIPTION: SEQ ID NO: 22:

```
TTT TAT ATC ACA GAT CTG CCA AAT GGG TTT CAT                    33
Phe Tyr Ile Thr Asp Leu Pro Asn Gly Phe His
 1               5                  10
```

(2) INFORMATION FOR SEQ ID NO: 23:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 23:

```
Phe Tyr Ile Thr Asp Leu Pro Asn Gly Phe His
 1               5                  10
```

(2) INFORMATION FOR SEQ ID NO: 24:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..27

(xi) SEQUENCE DESCRIPTION: SEQ ID NO: 24:

```
GTG GGA AGA AAC ATA AGC TTT GTA TAC                            27
Val Gly Arg Asn Ile Ser Phe Val Tyr
 1               5
```

(2) INFORMATION FOR SEQ ID NO: 25:

(i) SEQUENCE CHARACTERISTICS:
        (A) LENGTH: 9 amino acids
        (B) TYPE: amino acid
        (D) TOPOLOGY: linear

```
        (ii) MOLECULE TYPE: protein (xi) SEQUENCE DESCRIPTION: SEQ ID NO: 25:

Val Gly Arg Asn Ile Ser Phe Val Tyr
 1               5

(2) INFORMATION FOR SEQ ID NO: 26:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (ix) FEATURE:
            (A) NAME/KEY: CDS
            (B) LOCATION: 1..30

(xi) SEQUENCE DESCRIPTION: SEQ ID NO: 26:

ATT ACA ATC AGA TCT CAG GAA GCA CCA TAC                           30
Ile Thr Ile Arg Ser Gln Glu Ala Pro Tyr
 1               5                  10

(2) INFORMATION FOR SEQ ID NO: 27:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO: 27:

Ile Thr Ile Arg Ser Gln Glu Ala Pro Tyr
 1               5                  10

(2) INFORMATION FOR SEQ ID NO: 28:

(i) SEQUENCE CHARACTERISTICS:
            (A) LENGTH: 28 base pairs
            (B) TYPE: nucleic acid
            (C) STRANDEDNESS: unknown
            (D) TOPOLOGY: unknown (ii) MOLECULE TYPE: DNA (ix) FEATURE:
            (A) NAME/KEY: CDS
            (B) LOCATION: 2..28

(xi) SEQUENCE DESCRIPTION: SEQ ID NO: 28:

C CAG AAG AAA GAA ATT ACC GTA CGA GAT                             28
  Gln Lys Lys Glu Ile Thr Val Arg Asp
   1               5

(2) INFORMATION FOR SEQ ID NO: 29:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO: 29:

Gln Lys Lys Glu Ile Thr Val Arg Asp
 1               5
```

(2) INFORMATION FOR SEQ ID NO: 30:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..33

(xi) SEQUENCE DESCRIPTION: SEQ ID NO: 30:

```
CTC ACT GTT CAA GGT ACC TCG GAC AAG TCT AAT                    33
Leu Thr Val Gln Gly Thr Ser Asp Lys Ser Asn
 1               5                  10
```

(2) INFORMATION FOR SEQ ID NO: 31:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 31:

```
Leu Thr Val Gln Gly Thr Ser Asp Lys Ser Asn
 1               5                  10
```

(2) INFORMATION FOR SEQ ID NO: 32:

(i) SEQUENCE CHARACTERISTICS:
        (A) LENGTH: 1363 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 32:

```
Met Gln Arg Gly Ala Ala Leu Cys Leu Arg Leu Trp Leu Cys Leu Gly
 1               5                  10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
                35                  40                  45

Ile Ser Cys Arg Gly Gln His Pro Leu Glu Trp Ala Trp Pro Gly Ala
 50                  55                  60

Gln Glu Ala Pro Ala Thr Gly Asp Lys Asp Ser Glu Asp Thr Gly Val
 65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
                100                 105                 110

Tyr Lys Tyr Ile Lys Ala Arg Ile Glu Gly Thr Thr Ala Ala Ser Ser
                115                 120                 125

Tyr Val Phe Val Arg Asp Phe Glu Gln Pro Phe Ile Asn Lys Pro Asp
                130                 135                 140

Thr Leu Leu Val Asn Arg Lys Asp Ala Met Trp Val Pro Cys Leu Val
145                 150                 155                 160
```

```
Ser Ile Pro Gly Leu Asn Val Thr Leu Arg Ser Gln Ser Ser Val Leu
            165                 170                 175

Trp Pro Asp Gly Gln Glu Val Val Trp Asp Arg Arg Gly Met Leu
        180                 185                 190

Val Ser Thr Pro Leu Leu His Asp Ala Leu Tyr Leu Gln Cys Glu Thr
            195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
            245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
            275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
            325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
            355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
            405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
    435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Ile Ser Leu Asp Thr Trp Thr Glu Phe Val Glu
            500                 505                 510

Gly Lys Asn Lys Thr Val Ser Lys Leu Val Ile Gln Asn Ala Asn Val
            515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575
```

```
Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Leu Ile Phe Cys Asn Met
785                 790                 795                 800

Arg Arg Pro Ala Asn Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
        820                 825                 830

Tyr Asp Ala Ser Gln Trp Glu Phe Pro Arg Glu Arg Leu His Leu Gly
    835                 840                 845

Arg Val Leu Gly Tyr Gly Ala Phe Gly Phe Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Ser Ala Ser Glu His Arg Ala Leu Met Ser Glu
            885                 890                 895

Leu Lys Ile Leu Ile His Ile Gly Asn His Leu Asn Val Val Asn Leu
        900                 905                 910

Leu Gly Ala Cys Thr Lys Pro Gln Gly Pro Leu Met Val Ile Val Glu
    915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Ser Glu Gly Gly Ala
        980                 985                 990

Arg Arg Ala Ser Pro Asp Gln Glu Ala Glu Asp Leu Trp Leu Ser Pro
```

```
                995                1000               1005
Leu Thr Met Glu Asp Leu Val Cys Tyr Ser Phe Gln Val Ala Arg Gly
    1010               1015               1020

Met Glu Phe Leu Ala Ser Arg Lys Cys Ile His Arg Asp Leu Ala Ala
1025               1030               1035               1040

Arg Asn Ile Leu Leu Ser Glu Ser Asp Val Val Lys Ile Cys Asp Phe
                1045               1050               1055

Gly Leu Ala Arg Asp Ile Tyr Lys Asp Pro Asp Tyr Val Arg Lys Gly
                1060               1065               1070

Ser Ala Arg Leu Pro Leu Lys Trp Met Ala Pro Glu Ser Ile Phe Asp
                1075               1080               1085

Lys Val Tyr Thr Thr Gln Ser Asp Val Met Ser Phe Gly Val Leu Leu
                1090               1095               1100

Trp Glu Ile Phe Ser Leu Gly Ala Ser Pro Tyr Pro Gly Val Gln Ile
1105               1110               1115               1120

Asn Glu Glu Phe Cys Gln Arg Leu Arg Asp Gly Thr Arg Met Arg Ala
                1125               1130               1135

Pro Glu Leu Ala Thr Pro Ala Ile Arg Arg Ile Met Leu Asn Cys Trp
                1140               1145               1150

Ser Gly Asp Pro Lys Ala Arg Pro Ala Phe Ser Glu Val Leu Glu Ile
                1155               1160               1165

Leu Gly Asp Leu Leu Gln Gly Arg Gly Leu Gln Glu Glu Glu Glu Val
                1170               1175               1180

Cys Met Ala Pro Arg Ser Ser Gln Ser Ser Glu Glu Gly Ser Phe Ser
1185               1190               1195               1200

Gln Val Ser Thr Met Ala Leu His Ile Ile Gln Ala Asp Ala Glu Asp
                1205               1210               1215

Ser Pro Pro Ser Leu Gln Arg His Ser Leu Ala Ala Arg Tyr Tyr Asn
                1220               1225               1230

Trp Val Ser Phe Pro Gly Cys Leu Ala Arg Gly Ala Glu Thr Arg Gly
                1235               1240               1245

Ser Ser Arg Met Lys Thr Phe Glu Glu Phe Pro Met Thr Pro Thr Thr
                1250               1255               1260

Tyr Lys Gly Ser Val Asp Asn Gln Thr Asp Ser Gly Met Val Leu Ala
1265               1270               1275               1280

Ser Glu Glu Phe Glu Gln Ile Glu Ser Arg His Arg Gln Glu Ser Gly
                1285               1290               1295

Phe Ser Cys Lys Gly Pro Gly Gln Asn Val Ala Val Thr Arg Ala His
                1300               1305               1310

Pro Asp Ser Gln Gly Arg Arg Arg Pro Glu Arg Gly Ala Arg Gly
                1315               1320               1325

Gly Gln Val Phe Tyr Asn Ser Glu Tyr Gly Glu Leu Ser Glu Pro Ser
                1330               1335               1340

Glu Glu Asp His Cys Ser Pro Ser Ala Arg Val Thr Phe Phe Thr Asp
1345               1350               1355               1360

Asn Ser Tyr
```

(2) INFORMATION FOR SEQ ID NO: 33:

(i) SEQUENCE CHARACTERISTICS:
        (A) LENGTH: 1362 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 33:

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Ser Leu Lys Gly Thr Gln His Ile Met Gln Ala Gly Gln Thr Leu His
        35                  40                  45

Leu Gln Cys Arg Gly Glu Ala Ala His Lys Trp Ser Leu Pro Glu Met
    50                  55                  60

Val Ser Lys Glu Ser Glu Arg Leu Ser Ile Thr Lys Ser Ala Cys Gly
65                  70                  75                  80

Arg Asn Gly Lys Gln Phe Cys Ser Thr Leu Thr Leu Asn Thr Ala Gln
                85                  90                  95

Ala Asn His Thr Gly Phe Tyr Ser Cys Lys Tyr Leu Ala Val Pro Thr
            100                 105                 110

Ser Lys Lys Lys Glu Thr Glu Ser Ala Ile Tyr Ile Phe Ile Ser Asp
        115                 120                 125

Thr Gly Arg Pro Phe Val Glu Met Tyr Ser Glu Ile Pro Glu Ile Ile
    130                 135                 140

His Met Thr Glu Gly Arg Glu Leu Val Ile Pro Cys Arg Val Thr Ser
145                 150                 155                 160

Pro Asn Ile Thr Val Thr Leu Lys Lys Phe Pro Leu Asp Thr Leu Ile
                165                 170                 175

Pro Asp Gly Lys Arg Ile Ile Trp Asp Ser Arg Lys Gly Phe Ile Ile
            180                 185                 190

Ser Asn Ala Thr Tyr Lys Glu Ile Gly Leu Leu Thr Cys Glu Ala Thr
        195                 200                 205

Val Asn Gly His Leu Tyr Lys Thr Asn Tyr Leu Thr His Arg Gln Thr
    210                 215                 220

Asn Thr Ile Ile Asp Val Gln Ile Ser Thr Pro Arg Pro Val Lys Leu
225                 230                 235                 240

Leu Arg Gly His Thr Leu Val Leu Asn Cys Thr Ala Thr Thr Pro Leu
                245                 250                 255

Asn Thr Arg Val Gln Met Thr Trp Ser Tyr Pro Asp Glu Lys Asn Lys
            260                 265                 270

Arg Ala Ser Val Arg Arg Ile Asp Gln Ser Asn Ser His Ala Asn
        275                 280                 285

Ile Phe Tyr Ser Val Leu Thr Ile Asp Lys Met Gln Asn Lys Asp Lys
    290                 295                 300

Gly Leu Tyr Thr Cys Arg Val Arg Ser Gly Pro Ser Phe Lys Ser Val
305                 310                 315                 320

Asn Thr Ser Val Arg Val His Glu Asn Pro Phe Ile Ser Val Glu Trp
                325                 330                 335

Leu Lys Gly Pro Ile Leu Glu Ala Thr Ala Gly Asp Glu Leu Val Lys
            340                 345                 350

Leu Pro Val Lys Leu Ala Ala Tyr Pro Pro Pro Glu Phe Gln Trp Tyr
        355                 360                 365

Lys Asp Gly Lys Ala Leu Ser Gly Arg His Ser Pro His Ala Leu Val
    370                 375                 380

Leu Lys Glu Val Thr Glu Ala Ser Thr Gly Thr Tyr Thr Leu Ala Leu
385                 390                 395                 400
```

-continued

```
Trp Asn Ser Ala Ala Gly Leu Arg Arg Asn Ile Ser Leu Glu Leu Val
            405                 410                 415

Val Asn Val Pro Pro Gln Ile His Glu Lys Glu Ala Ser Ser Pro Ser
        420                 425                 430

Ile Tyr Ser Arg His Ser Arg Gln Ala Leu Thr Cys Thr Ala Tyr Gly
            435                 440                 445

Val Pro Leu Pro Leu Ser Ile Gln Trp His Trp Arg Pro Trp Thr Pro
    450                 455                 460

Cys Lys Met Phe Ala Gln Arg Ser Leu Arg Arg Gln Gln Gln Asp
465             470                 475                 480

Leu Met Pro Gln Cys Arg Asp Trp Arg Ala Val Thr Thr Gln Asp Ala
                485                 490                 495

Val Asn Pro Ile Glu Ser Leu Asp Thr Trp Thr Glu Phe Val Glu Gly
            500                 505                 510

Lys Asn Lys Thr Val Ser Lys Leu Val Ile Gln Asn Ala Asn Val Ser
        515                 520                 525

Ala Met Tyr Lys Cys Val Val Ser Asn Lys Val Gly Gln Asp Glu Arg
    530                 535                 540

Leu Ile Tyr Phe Tyr Val Thr Thr Ile Pro Asp Gly Phe Thr Ile Glu
545                 550                 555                 560

Ser Lys Pro Ser Glu Glu Leu Leu Glu Gly Gln Pro Val Leu Leu Ser
                565                 570                 575

Cys Gln Ala Asp Ser Tyr Lys Tyr Glu His Leu Arg Trp Tyr Arg Leu
            580                 585                 590

Asn Leu Ser Thr Leu His Asp Ala His Gly Asn Pro Leu Leu Leu Asp
        595                 600                 605

Cys Lys Asn Val His Leu Phe Ala Thr Pro Leu Ala Ala Ser Leu Glu
610                 615                 620

Glu Val Ala Pro Gly Ala Arg His Ala Thr Leu Ser Leu Ser Ile Pro
625                 630                 635                 640

Arg Val Ala Pro Glu His Glu Gly His Tyr Val Cys Glu Val Gln Asp
                645                 650                 655

Arg Arg Ser His Asp Lys His Cys His Lys Lys Tyr Leu Ser Val Gln
            660                 665                 670

Ala Leu Glu Ala Pro Arg Leu Thr Gln Asn Leu Thr Asp Leu Leu Val
        675                 680                 685

Asn Val Ser Asp Ser Leu Glu Met Gln Cys Leu Val Ala Gly Ala His
    690                 695                 700

Ala Pro Ser Ile Val Trp Tyr Lys Asp Glu Arg Leu Leu Glu Glu Lys
705                 710                 715                 720

Ser Gly Val Asp Leu Ala Asp Ser Asn Gln Lys Leu Ser Ile Gln Arg
                725                 730                 735

Val Arg Glu Glu Asp Ala Gly Arg Tyr Leu Cys Ser Val Cys Asn Ala
            740                 745                 750

Lys Gly Cys Val Asn Ser Ser Ala Ser Val Ala Val Glu Gly Ser Glu
        755                 760                 765

Asp Lys Gly Ser Met Glu Ile Val Ile Leu Val Gly Thr Gly Val Ile
    770                 775                 780

Ala Val Phe Phe Trp Val Leu Leu Leu Leu Ile Phe Cys Asn Met Arg
785                 790                 795                 800

Arg Pro Ala His Ala Asp Ile Lys Thr Gly Tyr Leu Ser Ile Ile Met
                805                 810                 815

Asp Pro Gly Glu Val Pro Leu Glu Glu Gln Cys Glu Tyr Leu Ser Tyr
```

-continued

```
                820             825             830
Asp Ala Ser Gln Trp Glu Phe Pro Arg Glu Arg Leu His Leu Gly Arg
            835             840             845
Val Leu Gly Tyr Gly Ala Phe Gly Lys Val Val Glu Ala Ser Ala Phe
850             855             860
Gly Ile His Lys Gly Ser Ser Cys Asp Thr Val Ala Val Lys Met Leu
865             870             875             880
Lys Glu Gly Ala Thr Ala Ser Glu His Arg Ala Leu Met Ser Glu Leu
            885             890             895
Lys Ile Leu Ile His Ile Gly Asn His Leu Asn Val Val Asn Leu Leu
            900             905             910
Gly Ala Cys Thr Lys Pro Gln Gly Pro Leu Met Val Ile Val Glu Phe
            915             920             925
Cys Lys Tyr Gly Asn Leu Ser Asn Phe Leu Arg Ala Lys Arg Asp Ala
            930             935             940
Phe Ser Pro Cys Ala Glu Lys Ser Pro Glu Gln Arg Gly Arg Phe Arg
945             950             955             960
Ala Met Val Glu Leu Ala Arg Leu Asp Arg Arg Arg Pro Gly Ser Ser
            965             970             975
Asp Arg Val Leu Phe Ala Arg Phe Ser Lys Thr Glu Gly Gly Ala Arg
            980             985             990
Arg Ala Ser Pro Asp Gln Glu Ala Glu Asp Leu Trp Leu Ser Pro Leu
            995             1000            1005
Thr Met Glu Asp Leu Val Cys Tyr Ser Phe Gln Val Ala Arg Gly Met
    1010            1015            1020
Glu Phe Leu Ala Ser Arg Lys Cys Ile His Arg Asp Leu Ala Ala Arg
1025            1030            1035            1040
Asn Ile Leu Leu Ser Glu Ser Asp Val Val Lys Ile Cys Asp Phe Gly
            1045            1050            1055
Leu Ala Arg Asp Ile Tyr Lys Asp Pro Asp Tyr Val Arg Lys Gly Ser
            1060            1065            1070
Ala Arg Leu Pro Leu Lys Trp Met Ala Pro Glu Ser Ile Phe Asp Lys
            1075            1080            1085
Val Tyr Thr Thr Gln Ser Asp Val Trp Ser Phe Gly Val Leu Leu Trp
            1090            1095            1100
Glu Ile Phe Ser Leu Gly Ala Ser Pro Tyr Pro Gly Val Gln Ile Asn
1105            1110            1115            1120
Glu Glu Phe Cys Gln Arg Leu Arg Asp Gly Thr Arg Met Arg Ala Pro
            1125            1130            1135
Glu Leu Ala Thr Pro Ala Ile Arg Arg Ile Met Leu Asn Cys Trp Ser
            1140            1145            1150
Gly Asp Pro Lys Ala Arg Pro Ala Phe Ser Glu Leu Val Glu Ile Leu
            1155            1160            1165
Gly Asp Leu Leu Gln Gly Arg Gly Leu Gln Glu Glu Glu Val Cys
            1170            1175            1180
Met Ala Pro Arg Ser Ser Gln Ser Ser Glu Glu Gly Ser Phe Ser Gln
1185            1190            1195            1200
Val Ser Thr Met Ala Leu His Ile Ala Gln Ala Asp Ala Glu Asp Ser
            1205            1210            1215
Pro Pro Ser Leu Gln Arg His Ser Leu Ala Ala Arg Tyr Tyr Asn Trp
            1220            1225            1230
Val Ser Phe Pro Gly Cys Leu Ala Arg Gly Ala Glu Thr Arg Gly Ser
            1235            1240            1245
```

```
Ser Arg Met Lys Thr Phe Glu Glu Phe Pro Met Thr Pro Thr Thr Tyr
    1250                1255                1260

Lys Gly Ser Val Asp Asn Gln Thr Asp Ser Gly Met Val Leu Ala Ser
1265                1270                1275                1280

Glu Glu Phe Glu Gln Ile Glu Ser Arg His Arg Gln Glu Ser Gly Phe
                1285                1290                1295

Ser Cys Lys Gly Pro Gly Gln Asn Val Ala Val Thr Arg Ala His Pro
            1300                1305                1310

Asp Ser Gln Gly Arg Arg Arg Pro Glu Arg Gly Ala Arg Gly Gly
            1315                1320                1325

Gln Val Phe Tyr Asn Ser Glu Tyr Gly Glu Leu Ser Glu Pro Ser Glu
        1330                1335                1340

Glu Asp His Cys Ser Pro Ser Ala Arg Val Thr Phe Phe Thr Asp Asn
1345                1350                1355                1360

Ser Tyr (2) INFORMATION FOR SEQ ID NO: 34:

(i) SEQUENCE CHARACTERISTICS:
        (A) LENGTH: 1368 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 34:

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Ser Ile Thr Thr Glu Glu Ser His Val Ile Asp Thr Gly Asp Ser Leu
            35                  40                  45

Ser Ile Ser Cys Arg Gly Gln His Pro Leu Glu Trp Ala Trp Pro Gly
50                  55                  60

Ala Gln Glu Ala Pro Ala Thr Gly Asp Lys Asp Ser Glu Asp Thr Gly
65                  70                  75                  80

Val Val Arg Asp Cys Glu Gly Thr Asp Ala Arg Pro Tyr Cys Lys Val
                85                  90                  95

Leu Leu Leu His Glu Val His Ala Asn Asp Thr Gly Ser Tyr Val Cys
            100                 105                 110

Tyr Tyr Lys Tyr Ile Lys Ala Arg Ile Glu Gly Thr Thr Ala Ala Ser
            115                 120                 125

Ile Tyr Ile Phe Ile Ser Asp Thr Gly Arg Pro Phe Val Glu Met Tyr
130                 135                 140

Ser Glu Ile Pro Glu Ile Ile His Met Thr Glu Gly Arg Glu Leu Val
145                 150                 155                 160

Ile Pro Cys Arg Val Thr Ser Pro Asn Ile Thr Val Thr Leu Lys Lys
                165                 170                 175

Phe Pro Leu Asp Thr Leu Ile Pro Asp Gly Lys Arg Ile Ile Trp Asp
            180                 185                 190

Ser Arg Lys Gly Phe Ile Ile Ser Asn Ala Thr Tyr Lys Glu Ile Gly
            195                 200                 205

Leu Leu Thr Cys Glu Ala Thr Val Asn Gly His Leu Tyr Lys Thr Asn
210                 215                 220
```

```
Tyr Leu Thr His Arg Thr Gly Asn Glu Leu Tyr Asp Ile Gln Leu Leu
225                 230                 235                 240

Pro Arg Lys Ser Leu Glu Leu Val Gly Glu Lys Leu Val Leu Asn
            245                 250                 255

Cys Thr Val Trp Ala Glu Phe Asn Ser Gly Val Thr Phe Asp Trp Asp
                260                 265                 270

Tyr Pro Gly Lys Gln Ala Glu Arg Gly Lys Trp Val Pro Glu Arg Arg
            275                 280                 285

Ser Gln Gln Thr His Thr Glu Leu Ser Ser Ile Leu Thr Ile His Asn
    290                 295                 300

Val Ser Gln His Asp Leu Gly Ser Tyr Val Cys Lys Ala Asn Asn Gly
305                 310                 315                 320

Ile Gln Arg Phe Arg Glu Ser Thr Glu Val Arg Val His Glu Asn Pro
                325                 330                 335

Phe Ile Ser Val Glu Trp Leu Lys Gly Pro Ile Leu Glu Ala Thr Ala
                340                 345                 350

Gly Asp Glu Leu Val Lys Leu Pro Val Lys Leu Ala Ala Tyr Pro Pro
            355                 360                 365

Pro Glu Phe Gln Trp Tyr Lys Asp Gly Lys Ala Leu Ser Gly Arg His
    370                 375                 380

Ser Pro His Ala Leu Val Leu Lys Glu Val Thr Glu Ala Ser Thr Gly
385                 390                 395                 400

Thr Tyr Thr Leu Ala Leu Trp Asn Ser Ala Ala Gly Leu Arg Arg Asn
                405                 410                 415

Ile Ser Leu Glu Leu Val Val Asn Val Pro Pro Gln Ile His Glu Lys
                420                 425                 430

Glu Ala Ser Ser Pro Ser Ile Tyr Ser Arg His Ser Arg Gln Ala Leu
            435                 440                 445

Thr Cys Thr Ala Tyr Gly Val Pro Leu Pro Leu Ser Ile Gln Trp His
    450                 455                 460

Trp Arg Pro Trp Thr Pro Cys Lys Met Phe Ala Gln Arg Ser Leu Arg
465                 470                 475                 480

Arg Arg Gln Gln Gln Asp Leu Met Pro Gln Cys Arg Asp Trp Arg Ala
                485                 490                 495

Val Thr Thr Gln Asp Ala Val Asn Pro Ile Glu Ser Leu Asp Thr Trp
            500                 505                 510

Thr Glu Phe Val Glu Gly Lys Asn Lys Thr Val Ser Lys Leu Val Ile
    515                 520                 525

Gln Asn Ala Asn Val Ser Ala Met Tyr Lys Cys Val Val Ser Asn Lys
530                 535                 540

Val Gly Gln Asp Glu Arg Leu Ile Tyr Phe Tyr Val Thr Thr Ile Pro
545                 550                 555                 560

Asp Gly Phe Thr Ile Glu Ser Lys Pro Ser Glu Glu Leu Leu Glu Gly
                565                 570                 575

Gln Pro Val Leu Leu Ser Cys Gln Ala Asp Ser Tyr Lys Tyr Glu His
            580                 585                 590

Leu Arg Trp Tyr Arg Leu Asn Leu Ser Thr Leu His Asp Ala His Gly
    595                 600                 605

Asn Pro Leu Leu Leu Asp Cys Lys Asn Val His Leu Phe Ala Thr Pro
    610                 615                 620

Leu Ala Ala Ser Leu Glu Glu Val Ala Pro Gly Ala Arg His Ala Thr
625                 630                 635                 640

Leu Ser Leu Ser Ile Pro Arg Val Ala Pro Glu His Glu Gly His Tyr
```

-continued

```
            645                 650                 655
Val Cys Glu Val Gln Asp Arg Arg Ser His Asp Lys His Cys His Lys
            660                 665                 670

Lys Tyr Leu Ser Val Gln Ala Leu Glu Ala Pro Arg Leu Thr Gln Asn
            675                 680                 685

Leu Thr Asp Leu Leu Val Asn Val Ser Asp Ser Leu Glu Met Gln Cys
            690                 695                 700

Leu Val Ala Gly Ala His Ala Pro Ser Ile Val Trp Tyr Lys Asp Glu
705                 710                 715                 720

Arg Leu Leu Glu Glu Lys Ser Gly Val Asp Leu Ala Asp Ser Asn Gln
                    725                 730                 735

Lys Leu Ser Ile Gln Arg Val Arg Glu Glu Asp Ala Gly Arg Tyr Leu
                    740                 745                 750

Cys Ser Val Cys Asn Ala Lys Gly Cys Val Asn Ser Ser Ala Ser Val
            755                 760                 765

Ala Val Glu Gly Ser Glu Asp Lys Gly Ser Met Glu Ile Val Ile Leu
            770                 775                 780

Val Gly Thr Gly Val Ile Ala Val Phe Phe Trp Val Leu Leu Leu Leu
785                 790                 795                 800

Ile Phe Cys Asn Met Arg Arg Pro Ala His Ala Asp Ile Lys Thr Gly
                    805                 810                 815

Tyr Leu Ser Ile Ile Met Asp Pro Gly Glu Val Pro Leu Glu Glu Gln
                    820                 825                 830

Cys Glu Tyr Leu Ser Tyr Asp Ala Ser Gln Trp Glu Phe Pro Arg Glu
            835                 840                 845

Arg Leu His Leu Gly Arg Val Leu Gly Tyr Gly Ala Phe Gly Lys Val
            850                 855                 860

Val Glu Ala Ser Ala Phe Gly Ile His Lys Gly Ser Ser Cys Asp Thr
865                 870                 875                 880

Val Ala Val Lys Met Leu Lys Glu Gly Ala Thr Ala Ser Glu His Arg
                    885                 890                 895

Ala Leu Met Ser Glu Leu Lys Ile Leu Ile His Ile Gly Asn His Leu
                    900                 905                 910

Asn Val Val Asn Leu Leu Gly Ala Cys Thr Lys Pro Gln Gly Pro Leu
            915                 920                 925

Met Val Ile Val Glu Phe Cys Lys Tyr Gly Asn Leu Ser Asn Phe Leu
            930                 935                 940

Arg Ala Lys Arg Asp Ala Phe Ser Pro Cys Ala Glu Lys Ser Pro Glu
945                 950                 955                 960

Gln Arg Gly Arg Phe Arg Ala Met Val Glu Leu Ala Arg Leu Asp Arg
                    965                 970                 975

Arg Arg Pro Gly Ser Ser Asp Arg Val Leu Phe Ala Arg Phe Ser Lys
                    980                 985                 990

Thr Glu Gly Gly Ala Arg Arg Ala Ser Pro Asp Gln Glu Ala Glu Asp
            995                 1000                1005

Leu Trp Leu Ser Pro Leu Thr Met Glu Asp Leu Val Cys Tyr Ser Phe
            1010                1015                1020

Gln Val Ala Arg Gly Met Glu Phe Leu Ala Ser Arg Lys Cys Ile His
1025                1030                1035                1040

Arg Asp Leu Ala Ala Arg Asn Ile Leu Leu Ser Glu Ser Asp Val Val
                    1045                1050                1055

Lys Ile Cys Asp Phe Gly Leu Ala Arg Asp Ile Tyr Lys Asp Pro Asp
                    1060                1065                1070
```

Tyr Val Arg Lys Gly Ser Ala Arg Leu Pro Leu Lys Trp Met Ala Pro
        1075                1080                1085

Glu Ser Ile Phe Asp Lys Val Tyr Thr Thr Gln Ser Asp Val Trp Ser
    1090                1095                1100

Phe Gly Val Leu Leu Trp Glu Ile Phe Ser Leu Gly Ala Ser Pro Tyr
1105                1110                1115                1120

Pro Gly Val Gln Ile Asn Glu Glu Phe Cys Gln Arg Leu Arg Asp Gly
            1125                1130                1135

Thr Arg Met Arg Ala Pro Glu Leu Ala Thr Pro Ala Ile Arg Arg Ile
        1140                1145                1150

Met Leu Asn Cys Trp Ser Gly Asp Pro Lys Ala Arg Pro Ala Phe Ser
        1155                1160                1165

Glu Leu Val Glu Ile Leu Gly Asp Leu Leu Gln Gly Arg Gly Leu Gln
        1170                1175                1180

Glu Glu Glu Glu Val Cys Met Ala Pro Arg Ser Ser Gln Ser Ser Glu
1185                1190                1195                1200

Glu Gly Ser Phe Ser Gln Val Ser Thr Met Ala Leu His Ile Ala Gln
            1205                1210                1215

Ala Asp Ala Glu Asp Ser Pro Pro Ser Leu Gln Arg His Ser Leu Ala
            1220                1225                1230

Ala Arg Tyr Tyr Asn Trp Val Ser Phe Pro Gly Cys Leu Ala Arg Gly
        1235                1240                1245

Ala Glu Thr Arg Gly Ser Ser Arg Met Lys Thr Phe Glu Glu Phe Pro
    1250                1255                1260

Met Thr Pro Thr Thr Tyr Lys Gly Ser Val Asp Asn Gln Thr Asp Ser
1265                1270                1275                1280

Gly Met Val Leu Ala Ser Glu Glu Phe Glu Gln Ile Glu Ser Arg His
            1285                1290                1295

Arg Gln Glu Ser Gly Phe Ser Cys Lys Gly Pro Gly Gln Asn Val Ala
        1300                1305                1310

Val Thr Arg Ala His Pro Asp Ser Gln Gly Arg Arg Arg Arg Pro Glu
        1315                1320                1325

Arg Gly Ala Arg Gly Gly Gln Val Phe Tyr Asn Ser Glu Tyr Gly Glu
        1330                1335                1340

Leu Ser Glu Pro Ser Glu Glu Asp His Cys Ser Pro Ser Ala Arg Val
1345                1350                1355                1360

Thr Phe Phe Thr Asp Asn Ser Tyr
            1365

(2) INFORMATION FOR SEQ ID NO: 35:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 35:

TCTAGAGAAT TCCATGGTCA GCTACTGGGA CACC                                           34

(2) INFORMATION FOR SEQ ID NO: 36:

(i) SEQUENCE CHARACTERISTICS:
        (A) LENGTH: 25 base pairs
        (B) TYPE: nucleic acid (C) STRANDEDNESS: unknown
        (D) TOPOLOGY: unknown (ii) MOLECULE TYPE: DNA (xi) SEQUENCE DESCRIPTION: SEQ ID NO: 36:

CCAGGTCATT TGAACTCTCG TGTTC                                              25

(2) INFORMATION FOR SEQ ID NO: 37:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 37:

TACTTAGAGG CCATACTCTT GTCCT                                              25

(2) INFORMATION FOR SEQ ID NO: 38:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 38:

GGATCCTTCG AAATTAGACT TGTCCGAGGT TC                                      32

(2) INFORMATION FOR SEQ ID NO: 39:

(i) SEQUENCE CHARACTERISTICS:
        (A) LENGTH: 61 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 39:

AAAATTAAAA GATCCAGATC TGACTATCTA TATATTTATT AGTGATACCG GTAGACCTTT        60

T                                                                        61

(2) INFORMATION FOR SEQ ID NO: 40:

(i) SEQUENCE CHARACTERISTICS:
        (A) LENGTH: 56 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 40

GAAGGAAACA GAAGGCGCCA TCTATATATT TATTCGAGGT ACCAATACAA TCATAG            56

(2) INFORMATION FOR SEQ ID NO: 41:

(i) SEQUENCE CHARACTERISTICS:
        (A) LENGTH: 63 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 41:

CAAACTATCT CACACATAGA TCTACCGTGC ATATATATGA TACCGGTTTC ATCACTGTGA          60

AAC                                                                      63

(2) INFORMATION FOR SEQ ID NO: 42:

(i) SEQUENCE CHARACTERISTICS:
        (A) LENGTH: 65 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 42:

GTTAACACCT CAGTGCACGT GTATGATGTC AATGTGAAAC CCCAGATCTA CGAAAAGGCC          60

GTGTC                                                                    65

(2) INFORMATION FOR SEQ ID NO: 43:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 43:

AAACCTCACT GCCACGCTAG CTGTCAATGT GTTTTATATC ACAGATCTGC CAAATGGGTT          60

TCAT                                                                     64

(2) INFORMATION FOR SEQ ID NO: 44:

(i) SEQUENCE CHARACTERISTICS:
        (A) LENGTH: 57 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 44:

GTGGGAAGAA ACATAAGCTT TGTATACATT ACAATCAGAT CTCAGGAAGC ACCATAC            57

(2) INFORMATION FOR SEQ ID NO: 45:

(i) SEQUENCE CHARACTERISTICS:
        (A) LENGTH: 61 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 45:

CCAGAAGAAA GAAATTACCG TACGAGATCT CACTGTTCAA GGTACCTCGG ACAAGTCTAA          60

T                                                                        61

(2) INFORMATION FOR SEQ ID NO: 46:

(i) SEQUENCE CHARACTERISTICS:

(A) LENGTH: 35 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 46:

CAGGTCAATC ATCGATGGTC AGCTACTGGG ACACC                                           35

(2) INFORMATION FOR SEQ ID NO: 47:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 47:

GGTCAACTAT TTCGAATTGT CGATGTGTGA GATAG                                           35

(2) INFORMATION FOR SEQ ID NO: 48:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 48:

GGTCAACTAT TTCGAATATA TGCACTGAGG TGTTAAC                                         37

(2) INFORMATION FOR SEQ ID NO: 49:

(i) SEQUENCE CHARACTERISTICS:
        (A) LENGTH: 93 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 49:

Pro Phe Val Glu Met Tyr Ser Glu Ile Pro Glu Ile Ile His Met Thr
1               5                   10                  15

Glu Gly Arg Glu Leu Val Ile Pro Cys Arg Val Thr Ser Pro Asn Ile
            20                  25                  30

Thr Val Thr Leu Lys Lys Phe Pro Leu Asp Thr Leu Ile Pro Asp Gly
        35                  40                  45

Lys Arg Ile Ile Trp Asp Ser Arg Lys Gly Phe Ile Ile Ser Asn Ala
    50                  55                  60

Thr Tyr Lys Glu Ile Gly Leu Leu Thr Cys Glu Ala Thr Val Asn Gly
65                  70                  75                  80

His Leu Tyr Lys Thr Asn Tyr Leu Thr His Arg Gln Thr
                85                  90

(2) INFORMATION FOR SEQ ID NO: 50:

(i) SEQUENCE CHARACTERISTICS:
        (A) LENGTH: 97 amino acids
        (B) TYPE: amino acid
        (C) STRANDEDNESS: unknown (D) TOPOLOGY: unknown (ii) MOLECULE TYPE: protein (xi) SEQUENCE DESCRIPTION: SEQ ID NO: 50:

Pro Phe Ile Ala Ser Val Ser Asp Gln His Gly Val Val Tyr Ile Thr
1               5                   10                  15

Glu Asn Lys Asn Lys Thr Val Val Ile Pro Cys Leu Gly Ser Ile Ser
                20                  25                  30

Asn Leu Asn Val Ser Leu Cys Ala Arg Tyr Pro Glu Lys Arg Phe Val
            35                  40                  45

Pro Asp Gly Asn Arg Ile Ser Trp Asp Ser Lys Lys Gly Phe Thr Ile
        50                  55                  60

Pro Ser Tyr Met Ile Ser Tyr Ala Gly Met Val Phe Cys Glu Ala Lys
65                  70                  75                  80

Ile Asn Asp Glu Ser Tyr Gln Ser Ile Met Tyr Ile Val Val Val Val
                85                  90                  95

Gly (2) INFORMATION FOR SEQ ID NO: 51:

(i) SEQUENCE CHARACTERISTICS:
            (A) LENGTH: 100 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 51:

Val Gln Ile Ser Thr Pro Arg Pro Val Lys Leu Leu Arg Gly His Thr
1               5                   10                  15

Leu Val Leu Asn Cys Thr Ala Thr Thr Pro Leu Asn Thr Arg Val Gln
                20                  25                  30

Met Thr Trp Ser Tyr Pro Asp Glu Lys Asn Lys Arg Ala Ser Val Arg
            35                  40                  45

Arg Arg Ile Asp Gln Ser Asn Ser His Ala Asn Ile Phe Tyr Ser Val
        50                  55                  60

Leu Thr Ile Asp Lys Met Gln Asn Lys Asp Lys Gly Leu Tyr Thr Cys
65                  70                  75                  80

Arg Val Arg Ser Gly Pro Ser Phe Lys Ser Val Asn Thr Ser Val His
                85                  90                  95

Ile Tyr Asp Lys
            100

(2) INFORMATION FOR SEQ ID NO: 52:

(i) SEQUENCE CHARACTERISTICS:
            (A) LENGTH: 102 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 52:

Val Val Leu Ser Pro Ser His Gly Ile Glu Leu Ser Val Gly Glu Lys
1               5                   10                  15

Leu Val Leu Asn Cys Thr Ala Arg Thr Glu Leu Asn Val Gly Ile Asp
                20                  25                  30

-continued

```
Phe Asn Trp Glu Tyr Pro Ser Ser Lys His Gln His Lys Lys Leu Val
        35                  40              45

Asn Arg Asp Leu Lys Thr Gln Ser Gly Ser Glu Met Lys Lys Phe Leu
    50                  55              60

Ser Thr Leu Thr Ile Asp Gly Val Thr Arg Ser Asp Gln Gly Leu Tyr
65              70                  75                  80

Thr Cys Ala Ala Ser Ser Gly Leu Met Thr Lys Lys Asn Ser Thr Phe
                85              90                  95

Val Arg Val His Glu Lys
            100
```